(12) United States Patent
Westwood et al.

(10) Patent No.: US 7,067,315 B2
(45) Date of Patent: Jun. 27, 2006

(54) IDENTIFICATION OF ANTI-PROTOZOAL AGENTS

(75) Inventors: Nicholas J. Westwood, Fife (GB); Gary E. Ward, Essex Junction, VT (US); Kimberly L. Carey, Jericho, VT (US); Timothy J. Mitchinson, Brookline, MA (US)

(73) Assignees: President and Fellows of Harvard College, Boston, MA (US); University of Vermont, Burlington, VT (US)

( * ) Notice: Subject to any disclaimer, the term of this patent is extended or adjusted under 35 U.S.C. 154(b) by 92 days.

(21) Appl. No.: 10/154,475

(22) Filed: May 22, 2002

(65) Prior Publication Data

US 2003/0113822 A1    Jun. 19, 2003

Related U.S. Application Data

(60) Provisional application No. 60/339,280, filed on Dec. 11, 2001, provisional application No. 60/292,805, filed on May 22, 2001.

(51) Int. Cl.
| | |
|---|---|
| C12N 5/06 | (2006.01) |
| C12N 5/16 | (2006.01) |
| C12Q 1/18 | (2006.01) |
| A61K 39/002 | (2006.01) |
| A61K 39/012 | (2006.01) |
| A61K 39/00 | (2006.01) |
| A61K 39/015 | (2006.01) |

(52) U.S. Cl. .................... 435/342; 435/32; 435/29; 424/265.1; 424/268.1; 424/269.1; 424/272.1; 424/273.1; 514/450; 514/452

(58) Field of Classification Search ............ 424/269.1, 424/267.1, 268.1, 270.1, 271.1, 272.1, 273.1; 435/7.1, 7.22, 32
See application file for complete search history.

(56) References Cited

U.S. PATENT DOCUMENTS

| | | | |
|---|---|---|---|
| 5,429,922 A | 7/1995 | Sibley et al. | 435/6 |
| 5,976,553 A | 11/1999 | Kim et al. | 424/271.1 |
| 6,313,090 B1 | 11/2001 | Rogers et al. | 514/2 |
| 6,329,157 B1 | 12/2001 | Maine et al. | 435/7.22 |
| 6,699,654 B1 * | 3/2004 | McLeod et al. | 435/4 |
| 6,737,237 B1 * | 5/2004 | McLeod et al. | 435/6 |
| 6,797,819 B1 * | 9/2004 | Shair et al. | 540/543 |
| 6,902,926 B1 * | 6/2005 | Ward et al. | 435/258.1 |
| 2001/0024798 A1 * | 9/2001 | Shair et al. | 435/7.1 |
| 2005/0142113 A1 * | 6/2005 | McLeod et al. | 424/93.2 |
| 2005/0210535 A1 * | 9/2005 | Ward et al. | 800/8 |
| 2005/0260224 A1 * | 11/2005 | Gillespie et al. | 424/191.1 |

FOREIGN PATENT DOCUMENTS

| | | | |
|---|---|---|---|
| WO | WO 99/64379 A2 * | 12/1999 | |
| WO | WO 99/66043 | 12/1999 | |
| WO | WO 02/095361 A2 * | 11/2002 | |
| WO | WO 2005/005430 A2 * | 1/2005 | |

OTHER PUBLICATIONS

Darkin-Rattray et al, PNAS USA, Nov. 1996, 93:13143-13147.*
Chio et al, Antimicrobial Agents and Chemotherapy, Mar. 1996, 40/3:727-733.*
Pfefferkorn et al, Antimicrobial Agents and Chemotherapy, Jan. 1994, 38/1:31-37.*
Barlin et al, Aust. J. Chem., 1990, 43:1367-1373.*
Carey et al, Mol. Biol. Cell, Nov. 2001, 12:271a, Abstract #1482 Abstract Only.*
Delarue et al, J. Med. Chem., 2001, 44:2827-2833.*
Ward et al, Cellular Microbiology, 2002, 4/8:471-482.*
Wichroski et al, Infection and Immunity, Aug. 2002, 70/8:4353-4361.*
Pelish et al, J. Am. Chem. Soc., 2001, 123:6740-6741.*
Ward et al, Experimental Parasitology, 1994, 79:480-487.*
Samuel et al, PNAS USA, 2003, 100/24:14281-14286.*
Augustine et al, International J. Parasitology, Jan. 2001, 31/1:1-8.*
Gornicki et al, International J. Parasitology, Aug. 2003, 33/9:885-896.*
Zhu et al, World Class Parasites, 2004, 8:153-163.*
Wiersma et al, International J. for Parasitology, 2004, 34:369-380.*
Mitchell et al, J. Parasitology, 2004, 90/3:639-642.*
Carey et al, PNAS, USA, May 11, 2004, 101/19:7433-7438.*
Hehl et al, Infection and Immunity, 2000, 68/12:7078-7086.*
Anders et al, Vaccine, 1998, 16(2/3):240-247.*
Lal et al, Infection and Immunity, 1996, 64/3:1054-1059.*
Brahimi et al, Infection and Immunity, 2001, 69/6:3845-3852.*

(Continued)

*Primary Examiner*—N. M. Minnifield
(74) *Attorney, Agent, or Firm*—Choate, Hall & Stewart, LLP

(57) ABSTRACT

The present invention provides novel assay systems and methods for monitoring cell invasion by protozoal parasites. The present invention further provides methods of using these assays systems to identify compounds that treat or prevent protozoal infection. The present invention further provides pharmaceutical compositions that have anit-protozoal activity and methods of treating infections.

11 Claims, 20 Drawing Sheets

OTHER PUBLICATIONS

Chatterjee et al, Infection and Immunity, 1995, 63/11:4375-4381.*
Malkin et al, Immunity and Infection, 2005, 73/6:3677-3685.*
Kwiatkowski et al, Lancet, 1997, 350:1696-1701.*
Lillehoj et al, Jpn. Poult. Sci., 2000, 37:117-141.*
Carruthers, et al., "Secretion of Micronemal Proteins is Associated with Toxoplasma Invasion of Host Cells", *Cellular Microbiology*, 1(3): 225-235, 1999.
Dobrowolski, et al., "Participation of Myosin in Gliding Motility and Host Cell Invasion by Toxoplasma Gondii", *Molecular Microbiology*, 26(1): 163-173, 1997.
Dobrowolski, et al., "Toxoplasma Invasion of Mammalian Cells Is Powered by the Actin Cytoskeleton of the Parasite", *Cell*, 84: 933-939, 1996.
Kieschnick, et al., "Toxoplasma Gondii Attachment to Host Cells is Regulated by a Calmodulin-Like Domain Protein Kinase", *The Journal of Biological Chemistry*, 276(15):12369-12377, 2001.
Wiersma, et al., "A Role for Coccidian cGMP-Dependent Protein Kinase in Motility and Invasion", *International Journal for Parasitology*, 34: 369-380, 2004.
International Search Report issued for corresponding PCT application PCT/US02/16448.

* cited by examiner

Invasion Inhibition

F3

84 µM: inhib.
42 µM: partial
21 µM: no effect

F3* no effect to 170 µM

G2

5 µM: inhib.
2.5 µM: partial

108296

244378

143055

143088

143267

157808

158661

156079

257557

258995

267405

217360

235234

235235

235236

130038

130084

169038

169039

119092

130103 
151231

151455 
151459

113070 
121904

146481 
173176

189129 
202240

238519

118793

137846

137861

101308

102260

104550

105249

107596

108343

112762

112799

134252

141852

144146

152813

154952

156579

158513

172077

175464

186318

230259

237717

249940

256729

104622

104694

115556

128045

136266

139598

144325

144939

152709

153753

157409

157591

160428

216862

244825

1L17
1N22

1L19

2F15

2B21
2B22

2C18

4E09
4D02

5F08

5D22

6C02

6C16

8D14

8D18

9B21

11D20

13B22

13B20

13B18

13B09

IDENTIFICATION OF ANTI-PROTOZOAL AGENTS

PRIORITY INFORMATION

The present application claims benefit of U.S. provisional patent application No. 60/292,805, filed May 22, 2001, U.S. patent application Ser. No. 09/863,141, filed May 22, 2001, and U.S. provisional patent application No. 60/339,280, filed Dec. 11, 2001. The entire contents of this application are hereby incorporated by reference in their entirety.

GOVERNMENT SUPPORT

Development of the present invention was funded by grants from the National Institutes of Health (GEW) (Grant Number K02 AI 01719 and Grant Number P01CA78048). Accordingly, the United States Government may have certain fights in the invention.

BACKGROUND OF THE INVENTION

Protozoa are unicellular eukaryotic microorganisms that lack cell walls and are usually motile and colorless. They are distinguished from algae by their lack of chlorophyll, from fungi by their motility and absence of a cell wall, and from slime molds by their lack of fruiting body formation.

Protozoa are generally classified into four major groups based on their life cycles or mechanisms of motility: the flagellates, the cilliates, the amoeba, and the sporozoa (or Apicomplexa). The flagellates are protozoa that employ from one to eight or so flagella for movement. The ciliates employ cilia, which are shorter than flagella and present in large numbers. Protozoa that move by extending pseudopodia are called amoeba. The fourth major group, the sporozoa or Apicomplexa, are non-motile, intracellular parasites (except during their sexual stage) that penetrate host cells by a mechanism involving their characteristic apical complex. Some protozoa do not fit into any of these four groups, such as the non-motile, intracellular microsporidia, which penetrate host cells by an injection mechanism.

Clinically important representatives of the flagellate group include *Giardia lamblia, Trichomonas vaginalis, Leishmania* spp., and *Trypanosoma* spp. *G. lamblia* is a waterborne intestinal parasite that occurs worldwide, causing diarrhea, and other intestinal symptoms. The most commonly used drugs used to treat giardiasis are metronidazole and other members of the 5-nitroimidazoles. Unfortunately, Metronidazole is mutagenic in the Ames test (Vogd et al., *Mutation Research*, vol. 26, 483–490 (1974)) and has various toxic side effects. In addition, the development of resistance to these drugs in *Giardia* and other protozoan parasites such as *Entamoeba histolytica* and *Trichomonas vaginalis* also limits their effectiveness. Leishmaniasis, a life-threatening disease caused by *Leishmania* spp., is a major health problem worldwide with an estimated 10–15 million people infected and 400,000 new cases each year. There is currently no satisfactory treatment for leishmaniasis. The treatment of choice is pentavalent antimony in the form of sodium stibogluconate or meglumine antimonate. Both drugs are administered intravenously, have severe adverse side effects, require hospitalization during treatment, and are not always effective (M. Ouelette and B. Papadopoulou, *Parasitology Today*, vol. 9, pp. 150–153 (1993)). *Trypanosoma* spp. cause life-threatening diseases in humans, including African sleeping sickness and Chagas disease, as well as a number of important diseases in domestic animals. *Leishmania* and *Trypanosoma* are closely-related genera, representing the major pathogens in the kinetoplastid group of protozoa.

The ciliates are generally non pathogenic, except for *Balantidium coli* which is an intestinal parasite of domestic animals, in particular, swine. Occasionally, *B. coli* infects humans, producing a severe dysentery.

The amoeba group includes the intestinal parasite *Entamoeba histolytica* that causes amoebic dysentery and extraintestinal abscesses of organs such as the liver and lung. The most commonly used drug for treating *E. histolytica* infection is metronidazole. Other free-living amoeba, which occasionally cause infections in humans, include *Acanthamoeba* and *Naegleria* spp.; these infections are typically difficult to treat.

The sporozoa (also known as Apicomplexan parasites) are a large group of protozoa, all of which are obligate parasites and the pathogenesis of the diseases they cause are directly due to repeated cycles of host cell invasion, growth, and host cell lysis. Representative sporozoas are the malaria parasite *Plasmodium* spp.; the human water-born pathogen of worldwide medical importance, *Cryptosporidium* spp.; *Toxoplasma gondii*; and several parasites veterinary importance including *Sarcocystis* spp.; *Theileria* spp.; *Babesia* spp.; and *Eimeria* spp. (causing coccidiosis in fowl and domestic animals). *Cryptosporidium parvum* is a common cause of intestinal infection leading to self-limited diarrhea, but in the immunocompromized individual *C. parvum* infection is chronic and life-threatening. There is currently no effective treatment for cryptosporidiosis.

The numerous Apicomplexan parasitic protozoans seriously impact human health, livestock health and the economy. Toxoplasmosis is among the most common parasitic diseases of man. Serosurveys suggest prevalence rates as high as 70–90% in many areas of both the developing and developed world. Between 10–45% of Americans become infected at some point in their lives. An infection in an individual with a competent immune system generally has minor or no symptoms. The infection tends to be self limiting, with the individual's immune system controlling and eliminating most of the parasites. Some parasites remain in bradyzoite form following acute infection and will be present in cysts in the central nervous system and muscle throughout the remainder of the individual's life.

*Toxoplasma gondii* is the causative agent in toxoplasmosis, an important disease in immunocompromised patients as well as congenitally-infected human fetuses. In contrast to the mild clinical symptoms of infection seen in a healthy individual with an intact immune system, subjects with weakened or otherwise compromised immune systems can have serious clinical effects from toxoplasma infection. In the fetus, toxoplasma infection can cause mental retardation, visual defects, and death. Toxoplasma infection can cause neurological damage, ocular lesions and death in adults with compromised immune systems, a group that includes for example individuals with HIV infection or patients undergoing immune-suppressive treatment for cancer.

*Toxoplasma gondii* is also pathogenic to animals, particularly sheep, in which it causes abortion, stillbirth, and fetal mummification. The pathology of toxoplasmosis in its human and animal hosts is a direct result of repeated cycles of host cell invasion, parasite replication, and host cell lysis. In addition, *Toxoplasma gondii* causes encephalitis, a dangerous life-threatening disease.

Acute toxoplasmosis can be difficult to treat. Sulfadiazine/pyramethamine is a regimen of choice, although side effects serious enough to warrant discontinuation of treatment are common. The toxic and potentially teratogenic effects of this regimen make management of the pregnant woman particularly problematic. AIDS patients require life-long suppressive therapy to prevent relapse, and as many as one third of the patients receiving suppressive sulfadiazine/ pyrimethamine therapy cannot tolerate the adverse side effects. For those who can tolerate the drugs, relapse occurs frequently. Pyrimethamine/clindamycin is a useful alternative therapy in AIDS patients who suffer an unusually high frequency of side effects from sulfa drugs. Unfortunately, this alternative combination can also cause considerable toxicity and is less effective at preventing relapse. Prevention of transmission through vaccination may, in some cases, be preferable to treatment, particularly for pregnant women and the immunocompromised.

The World Health Organization estimates that 300–500 million people are infected by malaria each year and that more than 2 million people, mostly women and children under the age of five, die from malaria annually. The disease has in recent years, made a dramatic comeback in regions where the disease was once eliminated or suppressed. *Plasmodium falciparum* causes a severe form of human malaria and is responsible for nearly all malaria-specific mortality. Resistance of *Plasmodium* to anti-malarial drugs is an increasingly serious problem in fighting the disease.

Other Apicomplexan parasitic infections also have severe clinical symptoms and may result in death of humans and livestock. Ticks transmit babesiosis, and although this is primarily a disease of animals, humans are also infected with this parasite. There are over 100 species of Babesia with *Babesia microti* and *Babesia divergens* the two most likely to cause human infection. *Babesia microti* is the organism responsible for a growing number of cases of infection especially in the northeast United States. Babesiosis is not only transmitted via tick bites, it can also be transmitted via blood transfusions, with documented cases of infection via this method.

*Sarcocystis* parasites may be ingested by humans in undercooked meat, and once in the body, they may form intestinal infections. More commonly, the sporocysts are ingested via fecal contamination, after which the sporocysts may result in cyst formation in striated muscle and cardiac muscle in the host.

Cryptosporidosis is a common infection in subjects with compromised immune systems such as AIDS patients and patients undergoing cancer therapy. Like sarcosporidiosis, the parasites are ingested via fecal contamination of oocysts, which release sporozoites that infect epithelial cells of the intestinal tract resulting in severe and at times life-threatening diarrheal disease. Although symptomatic infection is most likely in immunocompromised individuals, asymptomatic infection also occurs in immunocompetent subjects and the infection is easily passed between individuals.

*Theileria* infection results in disorders such as: East Coast Fever and Mediterranean Coast Fever, and is transmitted by ticks. Following infection, the parasites are located in the host's red blood cells and clinical symptoms include fever, weight loss, enlarged lymph nodes and spleen, mild anemia, and possible pulmonary involvement.

There are numerous species of Eimeria, and an oral/fecal route of transmission results in intestinal infection in cows, sheep, goats, pigs, ducks, chickens, turkeys, and rabbits, with the domestic chicken host to seven different species of *Eimeria*. Due to its widespread nature and its effects on the host animal, which may result in sub-optimal weight gain and reduced economic value, *Eimeria* is an economically important disease in modern poultry production. *Eimeria* is estimated to have resulted in losses of over 50 million dollars in the United States in 1986 alone.

Another phylum of protozoa, microsporidia, includes obligate, intracellular pathogens, which cause intestinal and systemic infections in immunocompromized patients, as well as economically important infections in fish and invertebrates. Microsporidiosis in patients suffering from acquired immune deficiency syndrome (AIDS) is primarily associated with *Encephalitozoon* species (including *E. intestinalis, E. cuniculi*, and *E. hellem*) and *Enterocytozoon bieneusi*. Microsporidiosis is a frequent cause of chronic diarrhea in AIDS patients and may also be found outside of the intestine in the eye, biliary tract, nasal sinuses, urinary tract and respiratory tract.

It will be appreciated that there is an urgent need for new chemotherapeutic agents to combat protozoal parasites, which are sufficiently effective, do not have harmful side effects, and are not difficult or expensive to administer. Preferably, the anti-protozoal compounds are active against a broad spectrum of protozoa, while remaining non-toxic to human and other mammalian cells. However, although high-throughput screening assays are playing an increasingly important role in the identification of therapeutic compounds as well as compounds that are useful in biological research, high-throughput screening assays are rare in the field of parisitology, usually due to the complex life cycle of the parasite and the experimental intractability of the system. Current approaches often rely on classical genetic systems, e.g., the identification of temperature sensitive mutants, inducible promoters and the like. Clearly, in order to identify the much needed anti-protozoal agents, there is a need for improved assay systems for identifying these agents. Such assay systems are provided herein below.

SUMMARY OF THE INVENTION

The invention provides assay systems and methods of using these assay systems for screening compounds for anti-protozoal activity. In one embodiment, the present invention provides cell-based assay systems capable of measuring the ability of a parasite to invade a cell. In certain preferred embodiments the assay systems provide cells, labeled parasites, and a means for detecting parasites that do not infect the cells. In related embodiments, the invention provides methods of detecting invasion of a cell by a protozoal parasite. In other related embodiments, the present invention provides methods of using the assay systems of the invention to identify compounds that affect (increase or decrease) the ability of a parasite to invade a cell. Particularly preferred methods include methods of using the assay system to screen compounds for anti-protozoal activity. It will be appreciated that the assay systems of the invention may also identify compounds that affect any phase of the life cycle of the protozoa, or affect protozoal motility.

The present invention further provides pharmaceutical compositions including anit-protozoal agents and method of using such pharmaceutical compositions to treat microbial infections and/or disorders related to microbial infections. The compounds can be used in combination with other agents for the prophylaxis and treatment of conditions associated with protozoal infections and/or disorders related to protozoal infections.

In certain preferred embodiments, anti-protozoal agents that are resistant to protozoal parasites, exhibit improved bioavailability, and/or have minimal side effects. In a particularly preferred embodiment of the invention, the anti-protozoal agents are effective against certain protozoal parasites that are resistant to some or even all of the antiprotozoal agents that are currently available or approved or in clinical trials.

The pharmaceutical compositions can be used alone or in combination with other agents for the prophylaxis and treatment of conditions associated with protozoal infections or disorders related to protozoal infections. In general, the inventive compositions include an effective amount of a compound or a pharmaceutically acceptable salt thereof, in combination with a pharmaceutically acceptable carrier, such as a diluent or excipient.

The present invention further provides, a combination therapy wherein an effective amount of an anti-protozoal agent, and an effective amount of one or more other compounds useful in the treatment of conditions associated with protozoal infections and/or disorders related to protozoal infections, are administered to a host or patient.

In yet another aspect, the present invention also provides a pharmaceutical pack or kit including one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration. The pharmaceutical pack or kit further provides novel assays for the identification of agents active against particular protozoal parasites, e.g., against malaria or toxoplasma. In certain embodiments the identified agents have broad spectrum activity against multiple classes of protozoal parasites, selected from or including flagellates, cilliates, amoeba, sporozoa, and microsproidia. In particular, these agents inhibit the ubiquitous aspects of protozoal cell invasion or motility.

In still another aspect, the invention provides methods for prophylaxis and/or treatment of conditions associated with protozoal infections and/or disorders related to protozoal infections by administering an effective amount of an anti-protozoal agent. In particular, the invention provides a method for the treatment or prophylaxis of conditions associated with protozoal infections and/or disorders related to protozoal infections by administering to a host (such as a, mammal (e.g., a human), bird, fish, or cell) or patient, such as a primate, an effective amount of a compound of the present invention.

More particularly, the compositions of the invention include pharmaceutical agents selected from the group of molecules provided in FIG. 6 (panels A–N) and a pharmaceutically acceptable carrier, wherein the pharmaceutical carrier is not dimethylsulfoxide (DMSO). In other preferred embodiments, the Apicomplexan inhibitor is one or more of the molecules provided in Table 1. below. In yet one embodiments, the enhancer of Apicomplexan parasite invasion is one or more of the molecules provided in Table 2. Preferred pharmaceutical agents of the invention include protozoal parasite inhibitors (Table 1). Certain preferred protozoal parasite inhibitors are Apicomplexan inhibitors. Particularly preferred Apicomplexan inhibitors of the invention are inhibitors of invasion. In certain embodiments, the Apicomplexan inhibitor is an Apicomplexan parasite toxin. According to the invention, Apicomplexan parasite toxins include external parasite toxins and internal parasite toxins. In other embodiments, the pharmaceutical agent is an enhancer of Apicomplexan parasite invasion (Table 2). According to the present invention, the Apicomplexan parasite is selected from the group consisting of: *Toxoplasma, Plasmodium, Eimeria, Theileria, Babesia, Sarcocystis*, and *Cryptosporidium*, and in other embodiments, the Apicomplexan parasite is *Toxoplasma gondii*.

Also provided by the invention are methods for treating a protozoal parasitic infection. In preferred embodiments, the subject is a mammal such as a human or an avian. The protozoal parasite is an Apicomplexan parasite, such as those described herein for example, *Toxoplasma, Plasmodium, Eimeria, Theileria, Babesia, Sarcocystis*, and *Cryptosporidium*. In certain preferred embodiments, the subject is infected with *Toxoplasma gondii*. The methods of treatment include administering to a subject in need of such treatment, an effective amount of an Apicomplexan parasite inhibitor to treat the Apicomplexan parasitic infection. In preferred embodiments, the Apicomplexan parasite inhibitor is one or more of the molecules provided in Table 1, below. In certain embodiments, the Apicomplexan inhibitor is an inhibitor of invasion. According to the invention, the Apicomplexan inhibitor is an Apicomplexan parasite toxin such as an external or internal parasite toxin.

According to yet another aspect of the invention, methods are provided for preventing a protozoal infection. In certain preferred embodiments, the subject is at risk of infection with an Apicomplexan parasite such as *Toxoplasma, Plasmodium, Eimeria, Theileria, Babesia, Sarcocystis*, and *Cryptosporidium*. In particularly preferred embodiments, the subject is at risk of infection with *Toxoplasma gondii*. According to the invention, the subject is a mammal such as a human or an avian. The methods include administering to a subject in need of such treatment, an effective amount of an Apicomplexan parasite inhibitor to prevent Apicomplexan parasitic infection. In certain preferred embodiments, the Apicomplexan parasite inhibitor is one or more of the molecules provided in Table 1. According to the present invention, the Apicomplexan inhibitor is an inhibitor of invasion. In certain embodiments, the Apicomplexan inhibitor is an Apicomplexan parasite toxin, for example, an external parasite or an internal parasite toxin.

According to another aspect of the invention, methods for treating a protozoal parasite infection are provided. In certain embodiments, the cell is infected with an Apicomplexan parasite such as *Toxoplasma, Plasmodium, Eimeria, Theileria, Babesia, Sarcocystis*, and *Cryptosporidium*. In some embodiments, the cell is infected with *Toxoplasma gondii*. According to the invention, the cell is a mammalian cell such as a human cell or an avian cell. In some embodiments, the cell is a cultured cell. The methods include administering to a cell in need of such treatment, an effective amount of an Apicomplexan parasite inhibitor to treat the Apicomplexan parasitic infection in the cell. In some embodiments, the Apicomplexan parasite inhibitor is one or more of the molecules provided in Table 1. In preferred embodiments, the Apicomplexan inhibitor is an inhibitor of invasion. In certain embodiments, the Apicomplexan inhibitor is an Apicomplexan parasite toxin such as an external or internal parasite toxin, as described herein.

According to yet another aspect of the invention, methods for preventing a protozoal parasitic infection are provided. In certain embodiments, the cell is at risk of infection with an Apicomplexan parasite such as *Toxoplasma, Plasmodium, Eimeria, Theileria, Babesia, Sarcocystis*, and *Cryptosporidium*. In certain embodiments, the cell is at risk of infection with *Toxoplasma gondii*. In other embodiments, the cell is a mammalian cell such as a human cell or an avian cell. In yet other embodiments, the cell is a cultured cell. The methods include administering to a cell in need of such treatment an effective amount of an Apicomplexan parasite inhibitor to prevent Apicomplexan parasitic infection in the cell. In preferred embodiments, the Apicomplexan parasite inhibitor is one or more of the molecules provided in Table 1. In certain preferred embodiments, the Apicomplexan inhibitor is an inhibitor of invasion. According to the invention, the Apicomplexan inhibitor is an external or internal Apicomplexan parasite toxin.

According to another aspect of the invention, methods for augmenting treatment of an Apicomplexan parasitic infection are provided. The methods include administering to a cell exposed to an Apicomplexan parasite an effective amount of an enhancer of Apicomplexan parasite invasion to augment an Apicomplexan parasitic infection. In some embodiments, the enhancer of Apicomplexan invasion is one or more of the molecules provided in Table 2. In certain embodiments, the cell is exposed to an Apicomplexan parasite such as *Toxoplasma, Plasmodium, Eimeria, Theileria, Babesia, Sarcocystis*, and *Cryptosporidia*. For example, the cell may be exposed to *Toxoplasma gondii*. According to certain embodiments the invention, the cell is a mammalian cell such as an avian cell or a human cell. In other embodiments, the cell is a cultured cell. In yet other embodiments, the cell is in a subject such as a mammal, or in a particular example an avian.

In other related embodiments, the present invention provides methods of processing a material contaminated with parasitic protozoa. Such methods include contacting the material with a protozoal parasite inhibitor to reduce the level of protozoal parasite contamination. In certain preferred embodiments, the protozoal parasite inhibitor is an Apicomplexan parasite inhibitor. In particularly preferred embodiments, the Apicomplexan parasite inhibitor is one or more of the molecules provided in Table 1. Preferably, the material is an aqueous material. In certain preferred embodiments, the material is drinking water. In other embodiments, the material includes blood, a body effusion, tissue, or cell. According to the present invention, the Apicomplexan inhibitor is an inhibitor of invasion that is an Apicomplexan parasite external or internal parasite toxin.

According to another aspect of the invention, methods of processing a material to prevent contamination with parasitic protozoa are provided. In certain preferred embodiments, the parasitic protozoa are Apicomplexan parasites. The methods include contacting the material with an Apicomplexan parasite inhibitor to prevent contamination with Apicomplexan parasitic protozoa. In preferred embodiments, the Apicomplexan parasite inhibitor is one or more of the molecules provided in Table 1. In certain embodiments the material is a aqueous material, for example drinking water. In other embodiments, the material includes blood, a body effusion, tissue, or cell. As described herein, the Apicomplexan inhibitor is an inhibitor of invasion, e.g. an external or internal Apicomplexan parasite toxin.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWING

The invention is described with reference to the several figures of the drawing, described below.

DEFINITIONS

Figure 1:
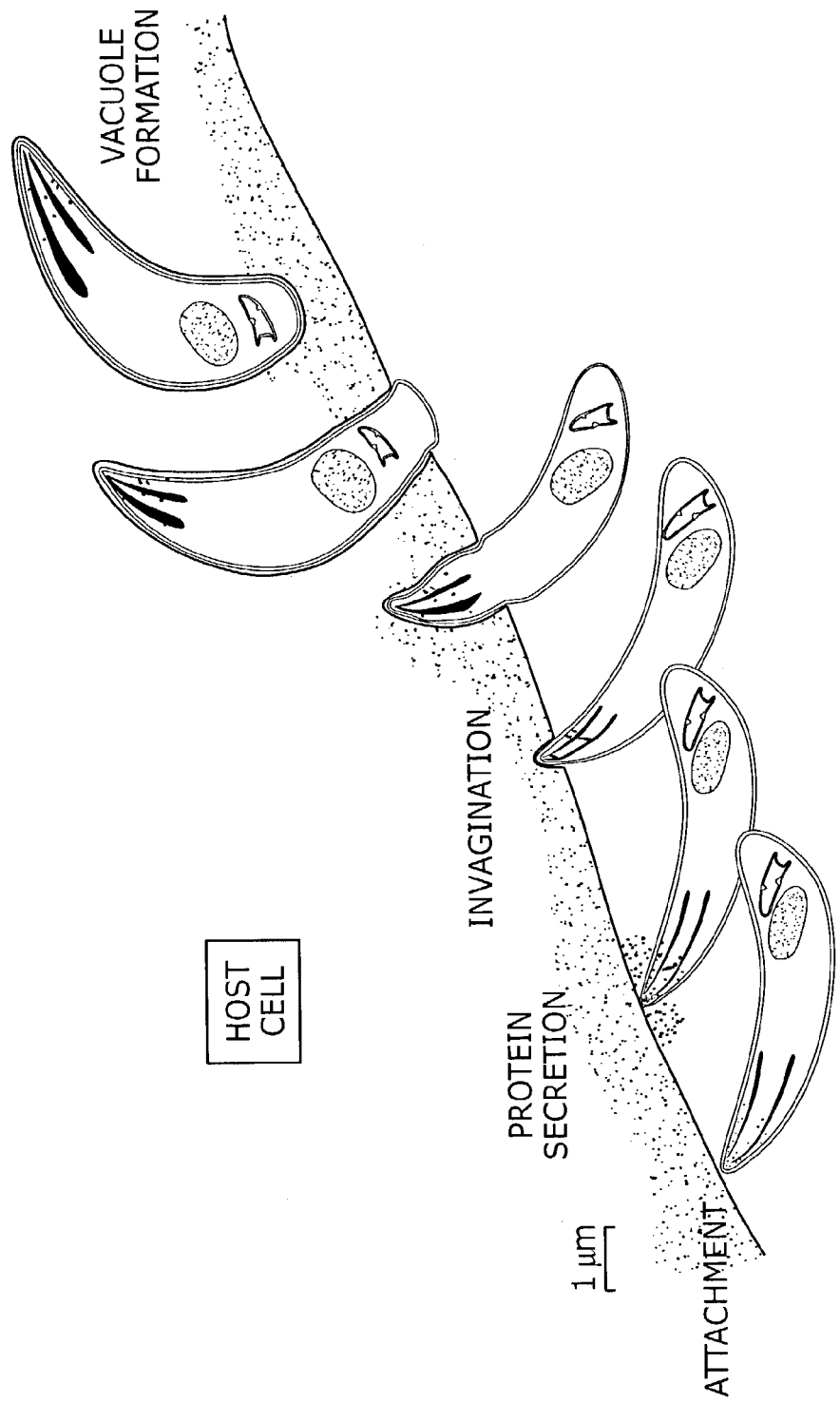
FIG. 1 is a schematic illustrating the invasion cycle of a host cell to the protozoa *Toxoplasma gondii*.

A "label" or a "detectable label" as used herein refers to a chemical moiety that is used to tag an entity, such as a cell, a protein, e.g., an antibody, so that it may be distinguished from another entity, thereby identifying the entity. According to the invention, labels used in a single assay system or assay method are preferably distinguishable from one another, i.e., are different from one another in their chemical structure. Furthermore, different labels used in a single assay system or method, due to their differing chemical structure also emit distinguishable signals. A label may be, for example, a fluorescent signal, a radioactive signal, an ultraviolet signal etc. Those skilled in the art will appreciate that a wide variety of labels and tags are available in the art (see for example, U.S. Pat. No. 6,027,890, incorporated herein by reference).

A "labeled protozoa" according to the invention, is a protozoal parasite that includes a detectable label. The detectable label may be either attached to the protozoal parasite, or rather, may be expressed by the protozoal parasite. The label allows detection of all protozoal parasites both internal and external to the cell. One labeled protozoal parasite, according to the invention, is a protozoal parasite that intracellularly expresses a fluorescent protein, e.g., green fluorescent protein, yellow fluorescent protein, or red fluorescent protein (see, e.g., Harpur et al. *Nat. Biotechnol.* 19(2):167–169 (2001); Mizuno et la. *Biochemistry* 40(8): 2502–2510 (2001); Huang et al. *Traffic* 2(5):345–357 (2001), each of which is incorporated herein by reference).

As discussed above, the present invention provides pharmaceutical compositions including compounds useful in the eradication or inactivation of harmful protozoal parasites. The pharmaceutical compositions may thus be utilized as therapeutic and/or disinfectant agents.

Additionally, it will be appreciated that pharmaceutically acceptable derivatives of the anti-protozoal compounds identified using the assay systems and methods described herein. Furthermore, the methods of treating animals (e.g., equines, bovines, felines, canines, swine, ovines, birds, insects, and humans) using these anti-protozoal compounds and pharmaceutical compositions thereof, or either of these in combination with one or more additional therapeutic agents as provided. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

For purposes of this invention, the chemical elements are identified in accordance with the Periodic Table of the Elements, CAS version, Handbook of Chemistry and Physics, 75$^{th}$ Ed., inside cover, and specific functional groups are defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

The term "treating", as used herein, unless otherwise indicated, means reversing, alleviating, inhibiting the progress of, or preventing a disorder or condition to which such term applies, or one or more symptoms of such disorder or condition caused by protozoal infection. The term "treatment", as used herein, refers to the act of treating, as "treating" is defined immediately above.

DETAILED DESCRIPTION OF CERTAIN PREFERRED EMBODIMENTS

The invention relates to assay systems and methods of using these assay systems for screening compounds for anit-protozoal activity. In one embodiment, the present invention provides cell-based assays to screen compounds for anit-protozoal activity.

The present invention further relates to pharmaceutical compositions including anti-protozoal compounds useful in the treatment and/or prevention of one or more protozoal infections. Those skilled in the art will appreciate that this includes compounds that inhibit the invasion of a cell by protozoal parasites, such as flagellates (*Giardia lamblia, Trichomonas vaginalis, Leishmania* spp., and *Trypanosoma* spp. *G. lamblia*), cilliates (e.g., *Balantidium coli*), amoebas (e.g., *Entamoeba histolytica, Acanthamoeba* spp., and *Naegleria* spp.), and sporozoas (Apicomplexa) (e.g., *Plasmodium* spp., *Cryptosporidium* spp., *Toxoplasma gondii, Sarcocystis* spp., *Theileria* spp., and *Eimeria* spp), microsporidia (*Encephalitozoon* species (including *E. intestinalis, E. cuniculi*, and *E. hellem*) and *Enterocytozoon bieneus*), and the like.

Assay Systems and Methods of Use

As noted above, the present invention relates to assay systems and methods of using theses assay systems to detect host cell invasion by intracellular protozoal parasites. The present invention further relates to methods of using the inventive assay systems to identify compounds capable of inhibiting host cell invasion by an intracellular protozoal parasite. One particular protozoa to which the assay systems and methods are amenable to is a protozoa of the Apicomplexa family of protozoa, *Toxoplasma gondii*. The present invention utilizes the experimentally accessible biological process of mammalian host cell invasion by the tachyzoite stage of *Toxoplasma gondii* to detect host cell invasion. The inventive assay systems and methods are further used to identify anti-protozoal compounds that inhibit motility of a protozoa.

Relatively little is known about the tachyzoite proteins that mediate host cell invasion. Many cytoskeletal, secretory, and surface proteins have been identified, but establishing a role for these proteins has been difficult, at least in part because disruption of a gene essential for invasion in a haploid, obligate intracellular parasite such as Toxoplasma is often lethal. The present assay system may be used to identify parasites having mutations in genes encoding proteins essential to invasion. Such mutant parasites will fail to invade the cell and will further fail to grow and replicate. The ability or inability of the parasite to invade a cell may be determined by detecting the number of parasites on the exterior vs. the interior of a host cell., as described herein.

The process of host cell invasion by *Toxoplasma gondii* initiates with the of attachment of the parasite to the host cell membrane (see FIG. 1). Once attached, the protozoa secretes a cocktail of proteins that initiate degradation of the cell wall. After the cell is permeated, invagination of the host cell begins and is complete when the parasite is entirely engulfed by the host cell. The process of vacuole formation is then initiated within the cell. The process of invasion is then complete and the parasite begins the process of replication inside the cell before it exits the cell and begins the invasion process again in other host cells.

The present invention provides methods of identifying compounds capable of inhibiting protozoal infection that can effect any stage of the Toxoplasma life cycle. In certain preferred embodiments, the present invention utilizes the host cell invasion cycle to determine the ability of a compound to effect the invasion process. One particular advantage of the inventive system is that perturbation of the invasion cycle is under the investigator's control. Any activating or inhibiting compound can be added to the cells at any time, making the assay system uniquely well-suited to the identification and study of essential cell invasion proteins. For example, chemical genetics refers to the systematic use of small molecules to activate or inactivate gene products as a way to determine gene function (T. J. Mitchison, *Chemistry & Biology*, 1:3–6 (1994); S. L. Schreiber, Bioor. *Med. Chem.*, 6:1127–1152 (1998)). Initial studies involve screening libraries of structurally diverse small molecules of compounds that generate a particular phenotype. These activating or inactivating compounds are then used to identify the targets that are responsible for generating the phenotype. Recent technological advances both in combinatorial chemistry and in high throughput screening have made the identification of small molecule/gene product pairs a feasible goal.

According to the present invention, the number of invading (internal) vs. external parasites is quantitated. Inhibitors of invasion are identified by having an increased number of parasites external to the cell, compared to cells in the absence of compound. Alternatively, a decrease in the number of internal parasites in the presence of compound, compared to the absence of compound, may also indicate the identification of an inhibitor of protozoal infection. Activators of invasion are identified by having an increased number of parasites internal to the cell, compared to cells in the absence of compound.

It is expected that identified compounds may effect an analogous biological process in other related, but less experimentally accessible Apicomplexan parasites (e.g., *Plasmodium, Cryptosporidium, Sarcocystis, Theileria, Babesia*, and *Eimeria*) and/or other less experimentally accessible protozoal parasites, such as flagellates, cilliates, amoebas, and microsporidia and thus be active in inhibiting intra cellular invasion of a broad range of protozoal parasites. That compounds may be discovered that have activity against multiple protozoa within a particular species of protozoa, or across multiple species of protozoa is supported by prior identification of a compound, cytochalsin D, which inhibits parasite motility and invasion in several Apicomplexan parasites by affecting actin filament dynamics in such as way as to lead to net actin filament depolymerization. Such anti-protozoal agents may be used as broad spectrum therapeutics, e.g., as anit-malarial or anti-toxoplasma agents. Alternatively, such anit-protozoal agents may be used for decontamination, e.g., decontamination of water having a high protozoal count.

In preferred embodiments, the present invention provides assay systems for analyzing parasitic invasion of a mammalian host cell. It will be appreciated that the assays of the invention may be adapted for detection of any of a number of parasites, including protozoa selected from the group consisting of flagellates, cilliates, the amoeba, and sporozoa or Ampicomplexan. In related embodiments, this assay is employed to identify compounds that affect (block or enhance) invasion of mammalian cells by a protozoal parasite. In particularly preferred embodiments, the present invention is directed to assay systems for measuring invasion of mammalian cells by the Apicomplexan parasite *Toxoplasma gondii* in vitro and use of such assay systems to identify compounds capable of affecting invasion of mammalian cells by *Toxoplasma gondii*. Although this particular embodiment exemplifies the assay systems and methods of the present invention, it should not be construed to limit the assay systems and methods of the invention to only this one particular parasite, as the inventive assay systems and more widely applicable.

The inventive assay systems utilize dual fluorescence to quantitate the number of parasites that have invaded a mammalian host cell. A first fluorescent signal is used to identify all protozoal parasites, e.g., all *Toxoplasma gondii* parasites, in the assay system that are both inside and outside the host cell. A second fluorescent signal is used to identify only the protozoal parasites that are external to the cell, e.g., parasites that have not invaded the host cell or parasites that have been blocked from invading the cell, e.g., by a compound that inhibits cell invasion.

Alternatively, the number of internal parasites may be quantitated by treating host cells with a non-cell permeable anti-protozoal agent that kills all of the external protozoal parasites, but does not kill any internal protozoal parasites; washing the host cells to remove the external killed parasites; and lysing the host cells. A culture is then taken of the lysed cells to quantitate the number of internal protozoal parasites capable of growing in the culture media. A decrease in the number of internal parasites in the presence of a compound compared to the absence of a compound indicates that the compound is an inhibitor of cell invasion.

Secondary or other screens may further be used to verify the compounds identified as inhibitors or activators of cell invasion. A subset of compounds that inhibit invasion may do so through inhibition of parasite motility. Assays for parasite motility, particularly *Toxoplasma gondii* motility, are well known in the art. One such assay is the SAG1 trial deposition assay for *Toxoplasma gondii*. This assay is used to measure movement of *Toxoplasma gondii* on a glass surface or over host cells by detecting the "slime trail" that these parasites leave behind them as they move. The trail is made of parasite membrane, which is rich in the protein SAG1, a dominant cell surface antigen of *Toxoplasma gondii*. Of course, it will be appreciated that antibodies to other surface proteins may also be used.

Once the compounds are verified using secondary assays, further biochemical and molecular techniques may be used to identify the targets of these compounds and to elucidate the specific roles that these target molecules play in the process of invasion. As but one example, the compound(s) may be labeled and contacted with a parasite to identify the host cell proteins with which these compounds interact. Such proteins may be purified, e.g., by labeling the compound with an immunoaffinity tag and applying the protein-bound compound to an immunoaffinity column.

In one preferred embodiment, the present invention provides assay systems for detecting invasion of a cell by a protozoa that include, a) a cell; b) a protozoa capable of infecting the cell; c) a first antibody comprising a first detectable label that is capable of binding to the protozoa; and d) a second antibody comprising a second detectable label that is capable of binding to the protozoa.

According to the present invention, the first and second antibodies may be the same antibody or may be different antibodies. For example, the first and second antibodies may be the anti-SAG1 antibody, specific for the SAG1 protein on the surface of *Toxoplasma gondii*. Alternatively, the antibodies may each be directed to a particular parasite, but may be directed to different surface proteins on the parasite. In another embodiment, the antibodies may each be directed to a different surface protein on one particular parasite. For example, SAG1 is one member of a family of parasite surface proteins known as SAGs. Indeed, dye conjugated antibodies to most of the members of this family would be useful in the present inventive assay to detect. *T. gondii*. The first and second detectable labels on the first and second antibodies of the invention, however, are distinguishable from one another, i.e., are different from one another. In general, according to the invention, the labels are distinguishable by chemical structure, and preferably emit a distinguishable signal, e.g., the first and second detectable labels emit two different fluorescent signals, e.g., red and green. Exemplary labels include fluorescent labels, radioactive labels, ultraviolet labels, mass top, and the like. Those skilled in the art will appreciate that a wide variety of labels are available in the art, see for example, U.S. Pat. No. 6,027,890, incorporated herein by reference.

In a related embodiment the present invention provides a method of using the assay system described above to detect invasion of a cell by a protozoa, that includes the steps of: a) contacting cells with a protozoal parasite for a time sufficient to allow invasion of the cells by the parasite; b) contacting protozoal parasites that are external to the cells with a first antibody that is capable of binding to the protozoa; c) permeabilizing the cells; d) contacting protozoal parasites that are external and internal to the cells with a second antibody that is capable of binding to the protozoal parasites; and e) detecting the first and second antibodies. The number of parasites invading the host cell is quantitated by subtracting the number of parasites detected by the first antibody (which detects parasites external to the cell) from the number of parasites detected by the second antibody (which detects the total number of parasites both internal and external to the cell).

The present invention also provides methods of screening any compound for its ability to affect the ability of a parasite to invade a cell by including in step a, of contacting cells with a protozoal parasite, a compound of interest. As described above, the compound of interest may be a compound from a library of compounds and the method is amenable to screening thousands of library compounds simultaneously, as described below.

A second assay system provided by the present invention is an assay system for detecting invasion of a cell by a protozoa, which includes a) a cell and a labeled protozoa capable of infecting the cell; and b) a means for detecting protozoa that do not invade the cell. By using labeled protozoa, the total number of protozoa internal and external to the cell are easily detected and quantitated (replacing the use of the second antibody in the first assay system above). The means for detecting protozoa the do not infect the cell, e.g., protozoa that are external to the cell, may be an antibody capable of binding to the protozoa.

In preferred embodiments, the labeled protozoan is a protozoan expressing a fluorescent protein. In certain preferred embodiments, the protozoan is a sporozoa expressing a fluorescent protein. For example, the examples provided below demonstrate use of *Toxoplasma gondii* expressing a yellow fluorescent protein. It will be appreciated that expression of proteins in protozoa is standard in the art, as demonstrated below (see also Sambrook et al., *Molecular Cloning: A Laboratory Manual*, Cold Spring Harbor Press, N.Y., Ausubel et al., *Current Protocols in Molecular Biology*, Greene Publishing Associates, New York, V. 1&2, 1996, each of which is incorporated by reference herein). Furthermore, it will be appreciated that a variety of fluorescent proteins (e.g., green, red, and yellow) are available in the art (see, e.g., Harpur et al. *Nat. Biotechnol.* 19(2): 167–169 (2001); Mizuno et la. *Biochemistry* 40(8): 2502–2510 (2001); Huang et al. *Traffic* 2(5):345–357 (2001)).

The antibodies of the inventive assay system preferably include a detectable label, such as the fluorescent labels described herein above. In one preferred embodiment the antibody binds the *Toxoplasma gondii* surface protein SAG1.

In a related embodiment, the present invention provides methods of using the second assay systems of the invention to detect invasion of a cell by a protozoa, by a) contacting cells with a labeled protozoal parasite for a time sufficient to allow invasion of the cells by the parasite; b) contacting protozoal parasites that are external to the cell with an antibody that is capable of binding to the protozoa; and c) detecting the number of protozoal parasites that are external to the cell.

As mentioned above, the assay systems and methods of the present invention are amenable to high throughput screening where several thousand compounds can be screened per day. For example, in one preferred embodiment, the fluorescent and immunofluorescent assays are carried out in a 384-well format. Digital fluorescence images are collected on a fully automated fluorescence microscope having an automated XY stage and a Z-motor that is required for computer controlled auto focusing, and the number of invading vs. external parasites quantitated automatically from the stored images (Metamorph® software by Universal Imaging). Positive results from the automated analysis are confirmed, e.g., by manual re-examination of individual wells under the microscope.

High-throughput screening provides an enormous advantage in the identification of Toxoplasma proteins that play a role in this process. The present high-throughput screening assay systems allow researchers to rapidly screen large numbers of compounds to identify key effectors of the life cycle of Toxoplasma. For example, the assay systems of the present invention can be used to identify compounds useful in chemical genetics. Identified effector compounds may assist in the identification of Toxoplasma proteins that function in invasion or other phases of the Toxoplasma life cycle. The effector compounds identified may also help elucidate a fundamental understanding of the mechanisms of host-parasite interaction. Alternatively or additionally, the compounds may be screened for therapeutic value and serve as therapeutic lead structures in the identification of additional anti-protozoal drugs.

It will be appreciated that any compound may be tested on any of the assay systems described herein and such testing may identify inhibitors or activities of cell invasion by a Toxoplasma gondii parasite. It will be appreciated that broad spectrum compounds may be identified that have activity toward *T. gondii* may also have activity towards other Apicomplexa family members sporozoa (Apicomplexa). Those skilled in the art will further appreciate that identified compounds may further be active against other protozoa, outside of the Apicomplexa family, e.g., fagellates, cilliates, amoebas, and microsporidia. Such compounds may be generated by any art available means.

In summary, the invention, in part, involves the use of methods to determine the functional activity of pharmaceutical agents described herein. An example, although not intended to be limiting, of a method with which the ability of a pharmaceutical agent to modulate a protozoal parasitic activity can be tested, is an in vitro assay system that utilizes dual fluorescence to quantitate the number of parasites that have invaded a mammalian host cell. Such an assay is described herein above (also see Examples). According to this aspect of the invention, a first fluorescent signal may be used to identify all protozoal parasites, e.g., all *Toxoplasma gondii* parasites, in the assay system that are both inside and outside the host cell. A second fluorescent signal may be used to identify only the protozoal parasites that are external to the cell, e.g., parasites that have not invaded the host cell or parasites that have been blocked from invading the cell, e.g., by a compound that inhibits cell invasion.

Alternatively, the number of internal parasites may be quantitated by treating host cells with a non-cell permeable anti-protozoal agent that kills all of the external protozoal parasites, but does not kill any internal protozoal parasites; washing the host cells to remove the external killed parasites; and lysing the host cells. A culture is then taken of the lysed cells to quantitate the number of internal protozoal parasites capable of growing in the culture media. A decrease in the number of internal parasites in the presence of a compound compared to the absence of a compound indicates that the compound is an inhibitor of cell invasion.

Secondary screens may further be used to verify the compounds identified as inhibitors or activators of cell invasion. A subset of compounds that inhibit invasion may do so through inhibition of parasite motility. Assays for parasite motility, particularly *Toxoplasma gondii* motility, are well known in the art such as the SAG1 trial deposition assay for *Toxoplasma gondii*. As described herein, this assay is used to measure movement of *Toxoplasma gondii* on a glass surface or over host cells by detecting the "slime trail" that these parasites leave behind them as they move. The trail is made of parasite membrane, which is rich in the protein SAG1, a dominant cell surface of *Toxoplasma gondii*. In some embodiments, antibodies of other surface proteins may also be used.

In addition to the in vitro assays described above, an in vivo assay may be used to determine the functional activity of pharmaceutical agents described herein. In such assays, animals may be exposed to protozoal parasites and treated with a pharmaceutical agent of the invention. Infection may be assayed by parasite load and/or survival of the experimental animals. In addition, measurements of infection may be utilized to assess activity, including antibody titer, and symptoms as described herein below. These measurements can then be compared to corresponding measurements in control animals. For example, test and control animals may be inoculated with parasite and serum samples may be drawn from the animals after the final inoculation (for example every one or two weeks after inoculation). Test animals also are administered a pharmaceutical agent of the invention and control animals are not. Serum from the animals can be analyzed for infection using known methods in the art as described herein below. Such assays may be used to compare levels of putative pharmaceutical agent to control levels of parasitic infection in an animal not administered the pharmaceutical agent as an indication that the putative pharmaceutical agent is effective to modulate protozoal parasitic infection.

The function or status of a pharmaceutical agent as a protozoal inhibitor or a protozoal enhancer, particularly an Apicomplexan inhibitor or as an Apicomplexan enhancer, can be determined according to assays known in the art or described herein. For example, cells can be contacted with a putative pharmaceutical agent and an Apicomplexan parasite, and standard procedures can be used to determine whether the parasite is inhibited in its ability to enter or infect the cells. Such methods may also be utilized to determine the status of analogs, variants, and derivatives as inhibitors of invasion or enhancers of invasion by protozoal parasites. One method for inhibiting infection is by inhibiting entry of protozoal parasites into cells. The ability to inhibit entry of protozoal parasites into cells with a putative pharmaceutical agent can be assessed using routine screening assays, e.g. by determining the level of entry of protozoal parasites into cells with and without the presence of the putative pharmaceutical agent.

Once the pharmaceutical agents are verified as modulating protozoal parasitic infection, particularly Apicomplexan parasitic infection, using secondary or other assays as described above herein, further biochemical and molecular techniques may be used to identify the targets of these compounds and to elucidate the specific roles that these target molecules play in the process of invasion. An example, though not intended to be limiting, is that the compound(s) may be labeled and contacted with a parasite to identify the host cell proteins with which these compounds interact. Such proteins may be purified, e.g., by labeling the compound with an immunoaffinity tag and applying the protein-bound compound to an immunoaffinity column.

In addition, the status of a pharmaceutical agent as a protozoal parasite toxin can be identified by using methods provided herein to determine the presence of a functional, active protozoal parasite. The agent may for example be assayed in the context of a material, for example a water sample, before and after contact with the sample and the pharmaceutical agent.

In another aspect of the invention, cell models and/or non-human animal models of protozoal infection may be produced by administering an enhancer of invasion to an animal or contacting a cell with the enhancer of invasion. Such models may be useful for testing treatment strategies, monitoring clinical features of disease, or as tools to assess prevention strategies of protozoal parasitic infection. Cells and animal models made using enhancing molecules of the invention may also be useful for assessing the ability of lead compounds to inhibit protozoal parasitic infection. For example, a cell contacted with an enhancer of invasion of the invention may be further contacted with putative agents that are candidate or lead compounds for treating or preventing Apicomplexan infection. The ability of the lead or candidate compound to prevent or treat the infection may be evaluated in the model cell or animal. In addition the enhancers may serve as valuable lead compounds in that if their targets (by definition functionally important) can be identified and characterized, it may subsequently be possible to rationally design new compounds that act as inhibitors of these targets.

Pharmaceutical Compositions

Generally, the present invention provides compounds useful for the treatment of protozoal infections (e.g., due to protozoal cell invasion) and/or disorders relating to a protozoal infection. It will be appreciated that the compounds of the present invention can exist in free form for treatment, or where appropriate, as a pharmaceutically acceptable derivative thereof. Additionally, it will be appreciated that one or more of the inventive compounds can be formulated with a pharmaceutically acceptable carrier or excipient to provide a pharmaceutical composition.

In certain preferred embodiments, the compounds will have activity against a broad range of protozoal agents. In other preferred embodiments, the compounds will be active against the compounds will have activity against Apicomplexan parasites (e.g., *Plasmodium, Cryptosporidium, Sarcocystis, Theileria, Babesia*, and *Eimeria*) as well as other less experimentally accessible protozoal parasites, such as flagellates, cilliates, amoebas, and microsporidia and thus be active in inhibiting intra cellular invasion of a broad range of protozoal parasites. According to the present invention, pharmacological agents are provided that are useful for the modulation of infection with Apicomplexan parasitic protozoa, such as *Toxoplasma, Plasmodium, Eimeria, Theileria, Babesia, Sarcocystis*, and *Cryptosporidium*. As used herein, the terms "Apicomplexan parasitic infection," refers to infection with any Apicomplexan parasitic protozoa. Apicomplexan parasitic protozoa include, but are not limited to: *Toxoplasma, Plasmodium, Eimeria, Theileria, Babesia, Sarcocystis*, and *Cryptosporidium*.

Treatment as it relates to the invention may be prophylactic or therapeutic. Prophylactic and therapeutic treatment may involve administering a pharmaceutical agent of the invention to modulate the protozoal parasite in the subject. In certain embodiments, the protozoal parasite is an Apicomplexan parasite. As used herein the term "modulate" means to alter an activity of the parasite with respect to a host. For example, modulation of an activity such as invasion into a cell may in some embodiments include inhibiting the entry or invasion of the protozoal parasite into the cell and in other embodiments include enhancing the entry of the protozoal parasite into the cell. In some embodiments, modulation of an activity of a protozoal parasite includes killing, injuring, or damaging the parasite. In some embodiments this occurs outside the cell and in other embodiments this occurs inside a cell.

As used herein a "subject" shall mean a human, vertebrate, or invertebrate animal including but not limited to a dog, cat, horse, cow, pig, sheep, goat, non-human primate (e.g. monkey), rabbit, rat, mouse, avian, arthropod (e.g. a tick) or insect (e.g. a mosquito).

As used herein, the term "cell" means a cell capable of being infected by, or suspected of being exposed to a protozoal parasite, e.g., an Apicomplexan parasite. This may include cells in or from a subject and cells grown in culture. A cell may also mean a cell collected from a subject such as a human or animal, for example, blood collected for purposes such as, but not limited to, transfusions. In some embodiments, a cell may be a negative control cell, which may be a cell that has not been exposed to a protozoal parasite. In some embodiments, a positive control cell may be a cell that has been exposed to a protozoal parasite but is free of a pharmaceutical agent of the invention. A cell is any cell that can be infected by a protozoal parasite, which includes, but is not limited to: mammalian cells, human cells, avian cells, insect cells, arthropod cells, neuronal cells, ocular cells, erythrocytes, lymphocytes, muscle cells, and intestinal cells.

One class of subjects according to the present invention is subjects having a protozoal parasitic infection. Such subjects are subjects in need of treatment with a protozoal inhibitor. This class of subjects includes subjects diagnosed with infection, exhibiting symptoms of infection, or having been exposed to a protozoal parasite. A subject at risk of developing a protozoal parasitic infection is a subject in need of prevention of infection. Such subjects include those at risk of exposure to an infection-causing protozoal parasite. For instance, a subject at risk may be a subject who is planning to travel to an area where a particular type of infectious protozoal parasite is found or it may be a subject who through lifestyle or medical procedures is exposed to bodily fluids which may contain a protozoal parasite or even any subject living in an area that a protozoal parasite has been identified. Subjects at risk of developing infection also include general populations to which a medical agency recommends preventative infectious measures for a particular infectious organism. In addition, immunocompromised persons are at a disproportional high risk for infections by opportunistic pathogens such as Toxoplasma and Cryptosporidium.

A subject may or may not exhibit symptoms of infection such as fever, swollen lymph glands, muscle aches, and pains. Methods to diagnose symptomatic and asymptomatic protozoal, e.g., Apicomplexan parasitic infection are known to those of ordinary skill in the medical arts and are described below herein. Some methods of diagnosis include, but are not limited to, blood tests for antibodies to the protozoal parasite and other assays such as lymph assays for protozoal parasites. Scans by computerized tomography (CT scan) or magnetic resonance imaging (MRI scan) may also be used in the diagnosis of some types of protozoal infection, for example brain scans for *Toxoplasma* infection.

INSERTDiagnostic tests known to those of ordinary skill in the art may be used to assess Apicomplexan parasitic infection status of a subject and to evaluate a therapeutically effective amount of a pharmaceutical agent administered. Examples of diagnostic tests are set forth below. A first determination of Apicomplexan parasitic infection may be obtained using one of the methods described below (or other methods known in the art), and a subsequent determination of infection may be done. A comparison of the infection levels may be used to assess the effectiveness of administration of a pharmaceutical agent of the invention as a prophylactic or a treatment of the Apicomplexan parasitic infection. Absence of an Apicomplexan parasitic infection may be an indication for prophylactic intervention by administering a pharmaceutical agent described herein to prevent Apicomplexan parasitic infection.

An example of a method of diagnosis of acute *Toxoplasma* infection involves assessing the levels of parasites remaining in the blood after exposure. This may be accomplished by isolation of the parasite from either blood or other body fluids after subinoculation of the body fluid into the peritoneal cavity of mice. (see Harrison's Principles of Internal Medicine, 14/e, McGraw Hill Companies, New York, 1998). If no parasites are found in the mouse's peritoneal fluid, its anti-*Toxoplasma* serum titer can be evaluated 4 to 6 weeks after inoculation. The presence of *Toxoplasma gondii* in a subject's body fluid represents an acute infection, and the presence of *Toxoplasma gondii* in tissue biopsies is an indication only of the presence of tissue cysts and not acute toxoplasmosis. (see Harrison's Principles of Internal Medicine, 14/e, McGraw Hill Companies, New York, 1998). Additional methods of diagnosis and assessment of chronic and acute toxoplasma infection are known to those of skill in the art.

In addition, diagnosis of an acute *Toxoplasma gondii* infection may be made by detection of the simultaneous presence of IgG and IgM antibody to *Toxoplasma* in the subject's serum. The Sabin-Feldman dye test, the indirect fluorescent antibody test, and the enzyme-linked immunosorbent assay (ELISA) all satisfactorily measure circulating IgG antibody to *Toxoplasma*. Positive IgG titers (>1:10) can be detected as early as 2 to 3 weeks after infection. These titers usually peak at 6 to 8 weeks and decline slowly to a new baseline level that persists for life. The methods currently available for this determination are the double-sandwich IgM-ELISA and the IgM-immunosorbent assay (IgM-ISAGA). The double-sandwich IgA-ELISA is more sensitive than the IgM-ELISA for detecting congenital infection in the fetus and newborn. (see Harrison's Principles of Internal Medicine, 14/e, McGraw Hill Companies, New York, 1998).

In addition to the diagnostic tests described above, clinical features of toxoplasma infection can be monitored for assessment of infection. These features include, but are not limited to: assessment of the presence of eye lesions, brain lesions, and brain inflammation. Such assessment can be with methods known to one of ordinary skill in the art, such as ophthalmologic testing, CSF evaluation, and radiologic studies. (see Harrison's Principles of Internal Medicine, 14/e, McGraw Hill Companies, New York, 1998).

Those of ordinary skill in the art know tests useful for diagnosis of other Apicomplexan parasitic infections. For example, diagnosis of malaria can be done by microscopic identification of asexual forms of the parasite in peripheral blood smears stained with Romanovsky staining, or Giemsa at pH 7.2, Wright's, Field's, or Leishman's stain. Both thin and thick blood smears may be examined. In addition, a finger-prick blood test is also available, in which the presence of *P. falciparum* histidine-rich protein 2 is determined. Additional methods of diagnosis and assessment of *Plasmodium* infection are known to those of skill in the art. The level of parisitemia may be important in the prognosis and can be determined with the above-identified diagnostic tests and by other means known in the art.

In addition to the diagnostic tests described above, clinical features of *Plasmodium* infection can be monitored for assessment of infection. Theses features include, but are not limited to: normochromic, nomocytic anemia, erythrocyte sedimentation rate, plasma viscosity, and platelet count may be reduced. Subjects may also have metabolic acidosis, with low plasma concentrations of glucose, sodium, bicarbonate, calcium, phosphate, and albumin together with elevations in lactate, blood urea nitrogen, creatinine, urate, muscle and liver enzymes, and conjugated and unconjugated bilirubin. In adults and children with cerebral malaria, the mean opening pressure at lumbar puncture is about 160 mm cerebrospinal fluid; the cerebrospinal fluid usually is normal or has a slightly elevated total protein level [<1.0 g/L (100 mg/dL)] (see Harrison's Principles of Internal Medicine, 14/e, McGraw Hill Companies, New York, 1998).

For *Eimeria* diagnosis, a lymph node biopsy smear and thick and thin blood films, may be performed.

A diagnostic procedure for Babesia may include examination of Giemsa-stained thick and thin blood films for small intraerythrocytic parasites. *Babesia* does not cause the production of pigment in parasites, nor are schizonts or gametocytes formed. An indirect immunofluorescence antibody test is useful for the diagnosis of infection with *B. microti* with serum antibody titer rising 2 to 4 weeks after the onset of illness and declining over 6 to 12 months. Another diagnostic assay involves the transfer of a bodily sample from a patient suspected of infection into a test animal. For instance, intraperitoneal inoculation of blood from patients with babesiosis into hamsters or gerbils results in detectable parasitemia within 2 to 4 weeks. (see Harrison's Principles of Internal Medicine, 14/e, McGraw Hill Companies, New York, 1998).

Sarcosporidiosis diagnosis may be based on the identification of sporocysts in the subject's stool or the identification of cysts measuring about 100 to 325 m in striated or cardiac muscle. Clinical symptoms may include muscle pain and swelling in humans. (see Harrison's Principles of Internal Medicine, 14/e, McGraw Hill Companies, New York, 1998).

*Cryptosporidium* diagnosis includes fecal examination for small oocysts, which are 4 to 5 m in diameter and are smaller than the fecal stages of most other parasites. Detection may be enhanced by techniques including modified acid-fast and direct immunofluorescent stains and enzyme immunoassays. If low numbers of oocysts are being excreted, Sheather's coverslip flotation method concentrates them for examination. Cryptosporidia also can be identified by light and electron microscopy at the apical surfaces of intestinal epithelium from biopsy specimens of the small bowel and, less frequently, the large bowel. (see Harrison's Principles of Internal Medicine, 14/e, McGraw Hill Companies, New York, 1998).

Diagnosis of *Theileria* may be done via identification of schizonts in superficial lymph nodes or spleen, using serodiagnosis, and/or the identification of piroplasms coincident with fever.

The identification of Apicomplexan parasites in or on an object, may be performed via standard diagnostic methods described above including microscopic examination, antibody labeling in a sample of the object, and by PCR analysis of a sample.

According to the present invention, a "pharmaceutical agent" is a compound selected from the group of compounds disclosed in FIG. 6 (panels A–N) and/or functionally active analogs, variants, and derivatives thereof. Functionally active analogs, variants, and derivatives of the compounds of FIG. 6 (panels A–N) include compounds that may have chemical substitutions, additions, and/or deletions but retain a biological function of the compounds of FIG. 6 (panels A–N). An example of such a function, although not intended to be limiting, is the ability to modulate protozoal parasitic infection. In preferred embodiments, the compounds have the ability to modulate Apicomplexan parasitic infection. An analog, variant, or derivative of a compound of FIG. 6 (panels A–N) may possess the same level of function as the compound of FIG. 6 (panels A–N) or may possess a reduced, or greater level of function (as compared to the compound of FIG. 6 (panels A–N)) depending on the modification.

The pharmaceutical agents of the invention include but are not limited to protozoal inhibitors and protozoal enhancers. In particularly preferred embodiments, the pharmaceutical agents of the invention include, for example, Apicomplexan inhibitors and Apicomplexan enhancers. An "Apicomplexan inhibitor" is a compound that inhibits the activity or function of an Apicomplexan parasite or kills the Apicomplexan parasite. Thus, Apicomplexan inhibitors include functional inhibitors, such as, inhibitors of invasion and toxins that kill the parasites.

As used herein, the term "inhibitor of invasion" means a pharmaceutical agent of the invention that reduces the entry of a protozoal parasite into a cell. In preferred embodiments, the term inhibitor or invasion means a pharmaceutical agent of the invention that reduces entry of an Apicomplexan parasite into a cell. Inhibitors of invasion include compounds from Table 1 and functional analogs, derivative, and variants thereof. Thus, inhibition of invasion means that the entry of a protozoal, e.g., Apicomplexan, parasite into a cell in the presence of inhibitor of invasion of the invention, would be reduced with respect to the level of entry in the absence of the inhibitor of invasion. The "inhibition of invasion" as used herein means prevention of entry into the cells by the protozoal parasite. It is not necessary to prevent all entry to lessen or prevent the manifestation of disease. Thus, the term "prevent" when used in this context refers to a reduction in entry by a parasite and/or the lack of further increase in entry, which would occur in the absence of the inhibitor.

TABLE 1

Inhibitors of Toxoplasma Invasion[1]

| Identification Number | Identification Number | Identification Number |
|---|---|---|
| IL17 | 2B22 | 4D02 |
| IN22 | 16E17 | 238519[3] |
| 1L19 | 109296 | 118793 |
| 2B21 | 244378 | 137846 |
| 2C18 | 143055 | 101308 |
| 2F15 | 143088[2] | 102260 |
| 4E09 | 143267[3] | 104550 |
| 5D22 | 157808 | 105249 |
| 5F08 | 158661 | 107596[3] |
| 6C02 | 156079 | 108343 |
| 8D14 | 257557 | 112799 |
| 8D18 | 258995 | 134252[3] |
| 9B21 | 267405 | 144146 |
| 13B20 | 217360 | 152813 |
| 13B22 | 235234 | 154952 |
| 14C15 | 235235 | 156579 |
| 14L23 | 235236 | 172077 |
| 15K6 | 130084 | 175464 |
| 15L5 | 169038[3] | 186318 |
| 16E2 | 169039 | 230259 |
| 16N08 | 119092[3] | 237717 |
| 13B16 | 130193 | 249940 |
| 16K05 | 151231 | 256729 |
| 6C16 | 151455 | 115556 |
| 13D16 | 151459 | 136266 |
| 11D20 | 113070 | 139598 |
| 13D19 | 121904 | 144325 |
| 13B09 | 173176 | 144939[3] |
| 13B18 | 189129 | 157591 |
| 16E3 | 202240 | 216862 |

[1]all inhibit toxoplasma, those tested for inhibition of Plasmodium are indicated.
[2]partial inhibitor of Plasmodium invasion, in addition to inhibitor of Toxoplasma invasion.
[3]inhibitor of Plasmodium invasion, in addition to inhibitor of Toxoplasma invasion.

A "protozoal parasite toxin," as used herein means a pharmaceutical agent of the invention that kills, injures, or damages the protozoal parasite, thereby inhibiting its ability to invade a cell or function within a cell. Protozoal parasite toxins include external and internal toxins. An external toxin is one that acts on the parasite prior to its entrance into a cell. An internal toxin is one that acts on the parasite once it is inside the cell. Some Apicomplexan parasite toxins function as both external and internal toxins. A particularly preferred protozoal parasite toxin of the invention is an Apicomplexan parasite toxin.

The invention permits the artisan to treat a subject having a protozoal parasitic infection or prevent a protozoal parasitic infection in a subject. Treatments include administering one or more pharmaceutical agents including the compounds of Table, and analogs, variants, and derivatives thereof, of the invention disclosed herein. Thus, in some embodiments, a protozoal inhibitor, such as an Apicomplexan inhibitor, of the invention is administered to treat or prevent infection in a subject. As used herein, the term "prevent infection" refers to a prophylactic treatment that increases the resistance of a subject to infection with a parasite or, in other words, decreases the likelihood that the subject will become infected with the parasite. The therapy may interfere with, reduce, or lower the level of entry into cells by the protozoal parasite. The terms "treat," "treated," or "treating," when used with respect to administration to a subject refers to a therapeutic regimen that decreases the amount or effect of an infectious agent in a subject who has become infected in order to fight the infection, e.g., reduce or eliminate the infection or prevent it from becoming worse, or which prevents a further increase in amount or activity of an infectious agent.

In some other aspects, the invention relates to a method of promoting infection of a subject or a cell with a protozoal parasite, e.g., an Apicomplexan parasite. This may be accomplished using an "enhancer of invasion," which as used herein is a pharmaceutical agent of the invention that augments the entry of a protozoal parasite into a cell. For example, enhancement of invasion means that the entry of a protozoal parasite into a cell in the presence of an enhancer of invasion of the invention would be increased with respect to the level of entry in the absence of the enhancer of invasion. Enhancers of invasion of the invention are provided in Table 2.

TABLE 2

Enhancers of Toxoplasma Invasion

| Identification Number | Identification Number |
|---|---|
| 2B03 | 112762 |
| 2F03 | 141852 |
| 2N03 | 158513 |
| 3C14 | 104622 |
| 3E05 | 104694 |
| 5C23 | 128045 |
| 6L11 | 152709 |
| 6M21a | 153753 |
| 6M21b | 157409 |
| 130038 | 160428 |
| 146481 | 244825 |
| 137861 | |

The pharmaceutical agent may be delivered to the cell using standard methods known to those of ordinary skill in the art. Various techniques may be employed for introducing pharmaceutical agents of the invention to cells, depending on whether the agents are introduced in vitro or in vivo in a host. In some embodiments of the invention, a pharmaceutical agent of the invention may be delivered in the form of a delivery complex. The delivery complex may deliver the pharmaceutical agent into any cell type, or may be associated with a means for targeting a specific cell type. Examples of pharmaceutical agent delivery complexes include agents associated with: a sterol (e.g., cholesterol), a lipid (e.g., a cationic lipid, virosome or liposome), or a target cell specific binding agent (e.g., a ligand recognized by target cell specific receptor). Some complexes may be sufficiently stable in vivo to prevent significant uncoupling prior to internalization by the target cell. However, the complex can be cleavable under appropriate conditions within the cell so that the pharmaceutical agent is released in a functional form.

An example of a targeting method, although not intended to be limiting, involves the use of liposomes to deliver a pharmaceutical agent of the invention into a cell. For certain uses, it may be desirable to target the agent to particular cells, for example erythrocytes. In such instances, a vehicle (e.g. a liposome) used for delivering a pharmaceutical agent of the invention into an erythrocyte may have a targeting molecule attached thereto that is antibody-specific for an erythrocyte surface membrane polypeptide or may have attached thereto a ligand for a receptor on the erythrocyte. Such a targeting molecule can be bound to or incorporated within the pharmaceutical agent delivery vehicle. Additional examples of targeting molecules are antibodies, including monoclonal antibodies. Where liposomes are employed to deliver the pharmaceutical agents of the invention, proteins that bind to a surface membrane protein associated with endocytosis may be incorporated into the liposome formulation for targeting and/or to facilitate uptake. Such proteins include capsid proteins or fragments thereof specific for a particular cell type, antibodies for proteins which undergo internalization in cycling, proteins that target intracellular localization and enhance intracellular half life, and the like.

In some aspects of the invention, functional analogs, derivatives, and variants of the compounds of FIG. 6 (panels A–N) can be made, for example, to enhance a property of a compound, such as stability. FIG. 6 (panels A–N) shows the chemical structures of the compounds identified by the Toxoplasma assay. Functional analogs, derivatives, and variants of the compounds of FIG. 6 (panels A–N) may also be made to provide a novel activity or property to a compound of FIG. 6 (panels A–N), for example, to enhance detection. In some embodiments of the invention, modifications to a protozoa, e.g., an Apicomplexan, modulating compound of the invention, can be made to the structure or side groups of the compound and can include deletions, truncations, substitutions, and additions of atoms, or side groups. Alternatively, modifications can be made by cleavage, addition of a linker molecule, addition of a detectable moiety, such as biotin or radioactive label, or substitution of one atom for another and the like.

The pharmaceutical agents of the invention also include, but are not limited to any pharmaceutically acceptable salts, esters, or salts of an ester, of a compound of FIG. 6 (panels A–N). Examples of salts of the pharmaceutical agents include, but are not limited to the salts provided in Table 3.

TABLE 3

Examples of pharmaceutical agent salts

| Identification Number | Salt |
|---|---|
| 271360 | Chloride salt |
| 235234 | Chloride salt |
| 235235 | Chloride salt |
| 235236 | Chloride salt |

TABLE 3-continued

Examples of pharmaceutical agent salts

| Identification Number | Salt |
|---|---|
| 130038 | Chloride salt |
| 130084 | Acetate salt |
| 137846 | Chloride salt |
| 137861 | Methanesulfonate salt |
| 102260 | Hydrochloride salt |
| 107596 | para-toluene sulfonate salt |
| 152813 | Chloride salt |
| 172077 | Chloride salt |
| 230259 | Chloride salt |
| 139598 | Chloride salt |

Derivatives of the compounds of FIG. 6 (panels A–N) include compounds that, upon administration to a subject in need of such administration, are capable of providing (directly or indirectly) a pharmaceutical agent as described herein. Examples of pharmaceutically acceptable derivatives of the invention include, but are not limited to, pro-drugs. A pro-drug is a derivative of a compound that contains an additional moiety that is susceptible to removal in vivo yielding the parent molecule as a pharmacologically active agent. An example of a pro-drug is an ester that is cleaved in vivo to yield a compound of interest. Pro-drugs of a variety of compounds, and materials and methods for derivatizing the parent compounds to create the pro-drugs are known to those of ordinary skill in the art and may be adapted to the present invention.

Analogs, variants, and derivatives of the compounds in FIG. 6 (panels A–N) of the invention may be identified using standard methods known to those of ordinary skill in the art. Useful methods involve identification of compounds having similar chemical structure, similar active groups, chemical family relatedness, and other standard characteristics. For the purposes of this invention, the chemical elements are identified in accordance with the Periodic Table of the Elements, CAS version, Handbook of Chemistry and Physics 75$^{th}$ Ed., inside cover, and specific functional groups are defined as described therein. Additionally, general principles of organic chemistry, as well as specific functional moieties and reactivity, are described in "Organic Chemistry", Thomas Sorrell, University Science Books, Sausalito. 1999, the contents of which are incorporated herein by reference in their entirety.

Using the structures of the compounds disclosed herein, one of ordinary skill in the art is enabled to make predictions of structural and chemical motifs for analogs, variants, and/or derivatives that possess similar functions of the compounds disclosed in FIG. 6 (panels A–N). Using structural motifs as search, evaluation, or design criteria, one of ordinary skill in the art is enabled to identify classes of compounds (functional variants of the protozoal modulating compounds, such as Apicomplexan modulating compounds) that have a reasonable likelihood of possessing the modulatory function of the compounds disclosed herein. These compounds may be synthesized and tested for activity as described herein.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier medium" means a nontoxic material that does not interfere with the effectiveness of the biological activity of the active ingredients. The characteristics of the carrier will depend on the route of administration. Pharmaceutically acceptable carrier mediums include any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anit-protozoal compounds of the invention, such as by producing any undesirable biological effect or otherwise interacting in a deleterious manner with any other component(s) of the pharmaceutical composition, its use is contemplated to be within the scope of this invention. In the pharmaceutical compositions of the invention, the active agent may be present in an amount of at least 0.1% and not more than 50% by weight based on the total weight of the composition, including carrier medium and/or auxiliary agent(s). Preferably, the proportion of active agent varies between 0.1 to 5% by weight of the composition. Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known carriers for medicaments may all be suitable as carrier media.

The compounds of the invention may be administered using any amount and any route of administration effective for attenuating infectivity of the protozoa. Thus, the expression "amount effective to attenuate infectivity of a protozoal parasite", as used herein, refers to a nontoxic but sufficient amount of the anit-protozoal agent to provide the desired treatment of protozoal infection. The exact amount required will vary from subject to subject, depending on the species, age, and general condition of the subject, the severity of the infection, the particular anit-protozoal agent, its mode of administration, and the like. The anit-protozoal compounds of the invention are preferably formulated in dosage unit form for ease of administration and uniformity of dosage. The expression "dosage unit form" as used herein refers to a physically discrete unit of anit-protozoal agent appropriate for the patient to be treated.

Each dosage should contain the quantity of active material calculated to produce the desired therapeutic effect either as such, or in association with the selected pharmaceutical carrier medium. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days. Typically, the anit-protozoal compounds of the invention will be administered in dosage units containing from about 5 mg to about 500 mg of the anit-protozoal agent with a range of about 0.1 mg to about 50 mg being preferred.

The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

The compounds of the invention may be administered orally, parenterally, such as by intramuscular injection, intraperitoneal injection, intranasal (aerosol), intravenous infusion, intracavity, subcutaneous, intradermal, or transdermal or the like, depending on the severity of the infection being treated. The compounds of the invention may be administered orally or parenterally at dosage levels of about 0.1 mg/kg to about 50 mg/kg and preferably from about 2 mg/kg to about 25 mg/kg, of patient body weight per day, one or more times a day, to obtain the desired therapeutic effect.

According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

As described above, the pharmaceutical compositions of the present invention additionally comprise a pharmaceutically acceptable carrier, which, as used herein, means a non-toxic, inert solid, semi-solid or liquid filler, diluent, encapsulating material or formulation auxiliary of any type. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, dextrose, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives (e.g., anti-microbials, anti-oxidants, chelating agents, and inert gases and the like) or buffers as may be required. Ophthalmic formulation, ear drops, and eye drops are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Uses of Compounds and Pharmaceutical Compositions

According to the methods of treatment of the present invention, protozoal infections are treated or prevented in a patient or organism such as an animal (e.g., humans, equines, bovines, felines, canines, swine, ovines), lower mammal, fish, bird, insects, or other organism, by administering to the patient a therapeutically effective amount of a compound or pharmaceutical composition of the invention, in such amounts and for such time as is necessary to achieve the desired result. In certain preferred embodiments, the compounds of the present invention are capable of acting as broad spectrum anti-protozoals and are effective against a range of protozoal parasites within a family of protozoal parasites (e.g., sporozoa), more preferably against protozoal parasites across multiple families of protozoal parasites (e.g., flagillates, cilliates, amoebas, sporozoa, and/or microsporidia). By a "therapeutically effective amount" of a compound of the invention is meant a sufficient amount of the compound to treat protozoal infections, at a reasonable benefit/risk ratio applicable to any medical treatment. It will be understood, however, that the total daily usage of the compounds and compositions of the present invention will be decided by the attending physician within the scope of sound medical judgment.

As discussed above and as exemplified in greater detail below, the compounds of the present invention are useful as anit-protozoal agents, and thus may be useful in the treatment or prevention of protozoal infections. As used herein, unless otherwise indicated, the terms or phrases "protozoal infection(s)", and "disorder relate to a protozoal infection" include, but are not limited to, the following, flagillates, cilliates, amoebas, sporozoa, and/or microsporidia.

In the case of treating an infectious disease, such as a protozoal infection, e.g., an Apicomplexan infection, the desired response is inhibiting the onset, stage, or progression of the disease or infection. This may involve slowing the progression of the disease temporarily, although more preferably, it involves halting the progression of the disease permanently. An effective amount for preventing infection is that amount that reduces the incidence of active infection when the cell or subject is exposed to the parasite, with respect to that amount that would occur in the absence of that agent.

In other embodiments of the invention, an effective amount of the pharmaceutical agent is that amount effective to enhance Apicomplexan parasitic infection. Such enhancements can be determined using standard assays as described above herein. Measurements of Apicomplexan parasitic infection, are known to those of ordinary skill in the art and may vary depending on the specific parasite.

It will be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-protozoal compound), or they may achieve different effects (for example, for prevention of infection, e.g., prevention of infection by the malaria parasite).

For example, the pharmaceutical agents of the invention may be administered alone, in combination with each other, and/or in combination with other anti-protozoal parasite drug therapies. Antitoxoplasma agents (for treatment and/or prophylaxis) that may be administered with pharmaceutical agents of the invention include, but are not limited to: pyrimethamine plus either sulfadiazine or clindamycin; trimethoprim; protein synthesis inhibitors such as clindamycin, chlortetracycline, and azithromycin; purine synthesis inhibitors such as arprinocid; atovaquone; spiramycin plus prednisone; Dapsone (diaminodiphenyl sulfone); macrolides including roxithromycin, clarithromycin, and azithromycin; and phenytoin.

Anti-malarial agents (for treatment and/or prophylaxis) that may be administered with pharmaceutical agents of the invention include, but are not limited to: mefloquine, doxycycline, chloroquine, aminoquinolines, dihydrofolate reductase inhibitors: pyrimethamine and proguanil (chloroguanide), dapsone, quinidine gluconate, quinine, artemisinin derivatives: artemether and artesunate, and primaquin.

Anti-babesia agents (for treatment and/or prophylaxis) that may be administered with pharmaceutical agents of the invention include, but are not limited to: quinine sulfate, clindamycin, Atovaquone suspension plus azithromycin. Severe infections with high-level *B. microti* parasitemia may also be treated with exchange transfusions in addition to quinine and clindamycin.

Anti-theileria agents (for treatment and/or prophylaxis) that may be administered with pharmaceutical agents of the invention include, but are not limited to tetracyclines, in an effort to arrest schizont formation. Anti-eimeria agents (for treatment and/or prophylaxis) that may be administered with pharmaceutical agents of the invention may include, but are not limited to butalex, menoctone, and tetracyclins.

The above-described drug therapies are known to those of ordinary skill in the art and are administered by modes known to those of skill in the art. The drug therapies are administered in amounts that are effective to achieve the physiological goals (to reduce protozoal parasite infection, and/or reduce protozoal parasite titer in a subject), in combination with the pharmaceutical agents of the invention. Certain drug therapies are administered in amounts that are effective to reduce Apicomplexan parasite infection, and/or reduce Apicomplexan parasite titer in a subject. Thus, it is contemplated that the drug therapies may be administered in amounts which are not capable of preventing or reducing the physiological consequences of the Apicomplexan parasitic infections when the drug therapies are administered alone, but which are capable of preventing or reducing the physiological consequences of Apicomplexan parasitic infection when administered in combination with the pharmaceutical agents of the invention.

The pharmaceutical agents of the invention may also be administered in conjunction with vaccine formulations administered to confer immunity to a subject at risk of exposure to protozoal, e.g., Apicomplexan, parasitic infection, which thereby prevents, reduces the severity of, or delays the onset of a subsequent protozoal parasitic infection.

In yet another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

In other aspects the invention involves preventing and/or treating Apicomplexan parasitic contamination of materials. A "material" as used herein is any liquid or solid material including, but not limited to: blood, tissue, bodily fluids, and tissue-processing equipment, including but not limited to: equipment for food processing, medical equipment, equipment for tissue transplant processing, and equipment for cell or bodily fluid processing. In some embodiments of the invention, the material is aqueous. In some embodiments, the material is water, an example of which, although not intended to be limiting, is drinking water. The invention also involves preventing and/or treating Apicomplexan parasitic contamination in blood, bodily fluids, cells, and tissue samples, including those from live human subjects and cadavers, as well as live animals and animal tissues and cells processed as food, cosmetics, or medication. As used herein, the term "contamination" means contact between the material and an Apicomplexan parasite.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance, which can be adapted to the practice of this invention in its various embodiments and the equivalents thereof.

EXAMPLES

Example I

Assay for Identifying Protozoal Inhibitors

This example describes methods for identifying small molecule inhibitors and activators using the inventive assay systems and methods for protozoal cell invasion.

Use of Labeled Protozoa

Figure 2:
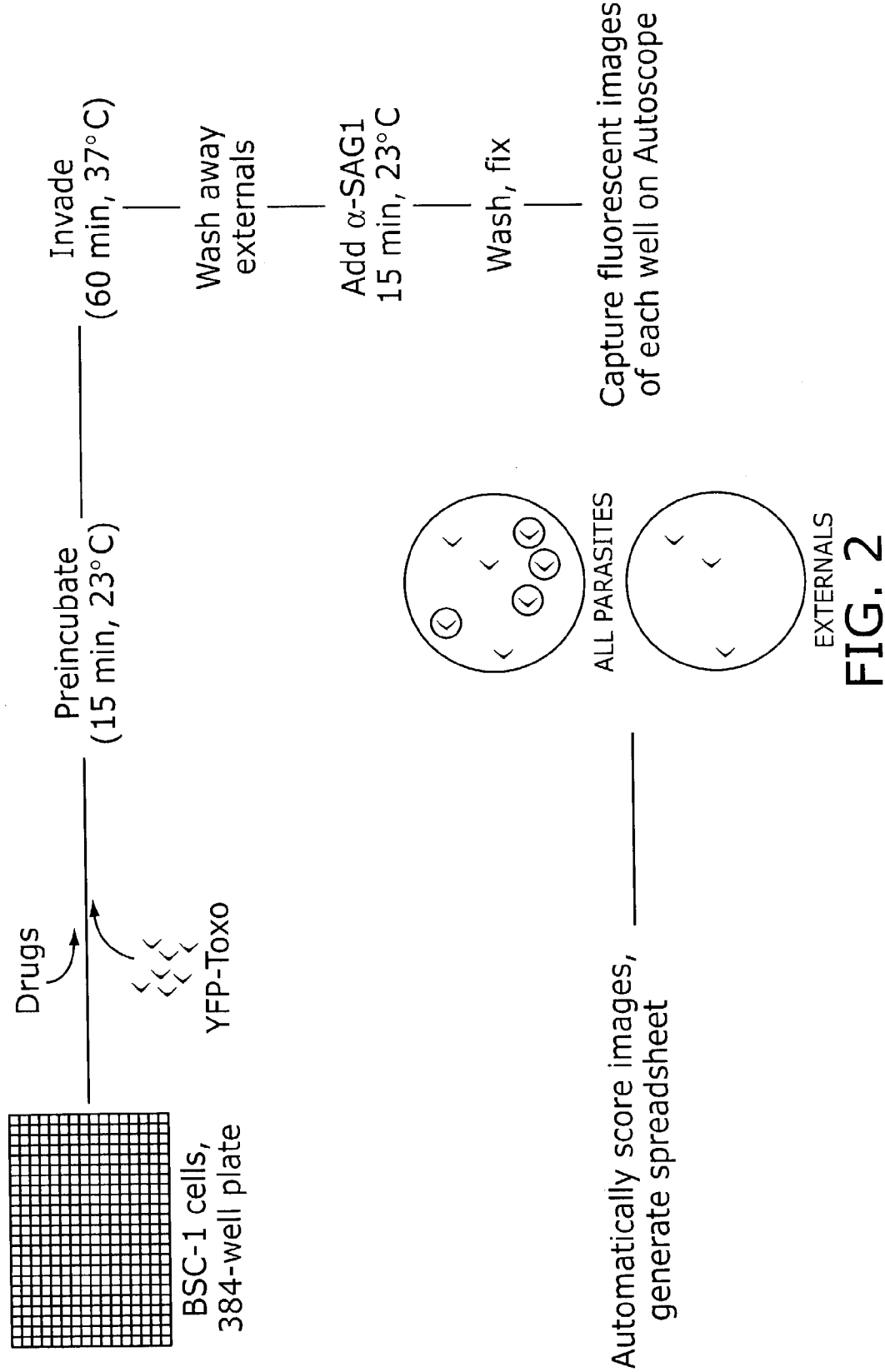
FIG. 2 is a flow chart illustrating a high throughput assay for host cell invasion by a protozoal parasite.

The following protocol is carried out in all wells of a 384 well plate, as illustrated in FIG. 2. The media covering a confluent monolayer of host cells is removed and replaced with a previously prepared solution of a test compound in media. The host cells are BSC-1 cells, a monkey kidney cell line (however, any host cell may be used since *Toxoplasma gondii* can invade essentially any nucleated cell). A solution of *T. gondii* tachyzoites (gift from Boris Striepen) expressing the yellow fluorescent protein is then added and the host cells and labeled parasites are preincubated with the compound at a temperature at which invasion does not occur (20–22 C). After 15 minutes the assay plate is temperature shifted to 37° C., a temperature at which host cell invasion by the parasites occurs in the absence of compound. After 1 hour, excess parasites are removed by repeat rounds of washing. External parasites are immunostained using dye-conjugated anti-SAG1 antibody. The dye is an Alexa dye (red) (Molecular Probes). The cells are then fixed by treating the cells for 30 minutes with formaldehyde/gluteraldehyde solution in Hanks buffer.

Automated image acquisition and analysis techniques are used to determine the number of invaded parasites. In order to quantitate invasion, the number of parasites inside the cell, which are yellow only, are counted. Alternatively, the total number of external parasites (which are both red and yellow) is subtracted from the total number of parasites, both internal and external (which are labeled yellow and red). Compounds that lower the invasion level by 80% or raise it (by 2 fold) compared to control values (cells+parasites in the absence of test compound) are considered as preliminary hits in this assay to be followed up with secondary screening.

Figure 3:
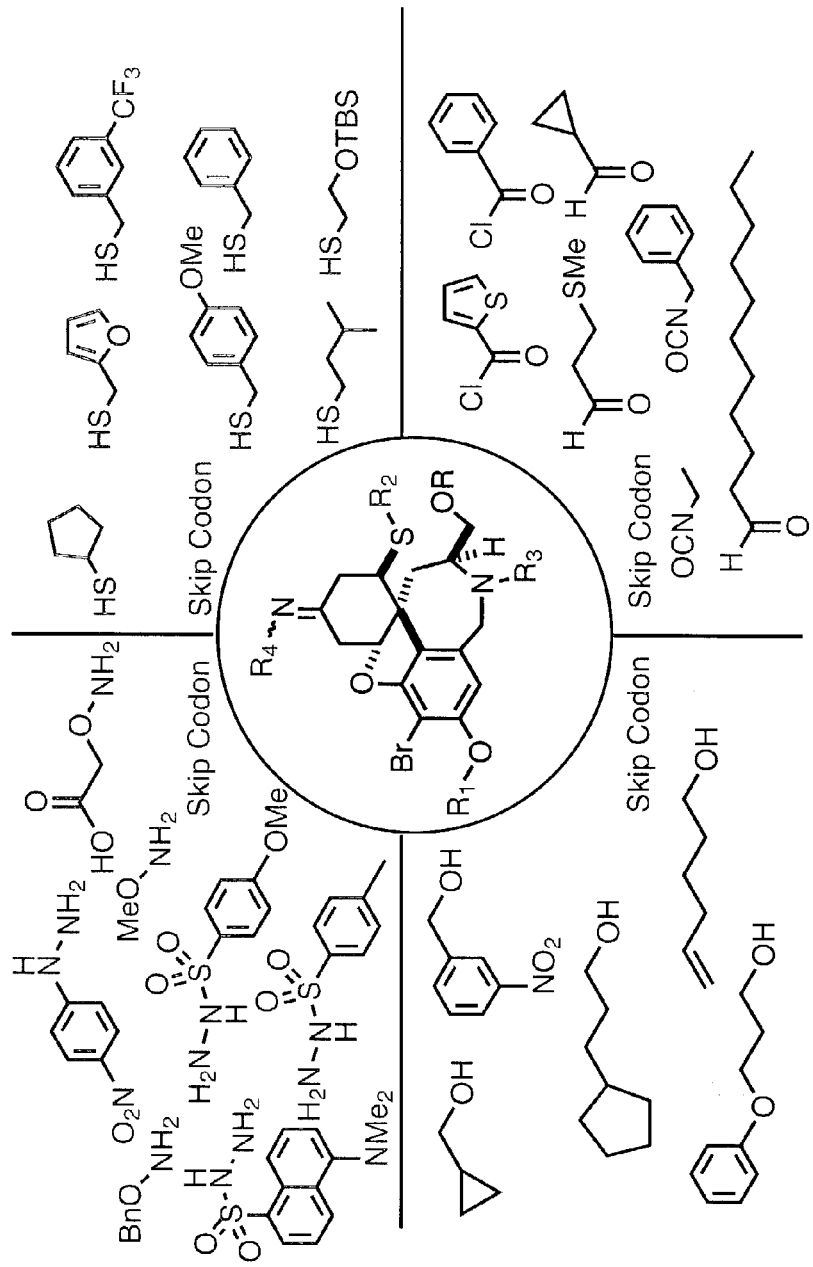
FIG. 3 is an illustration depicting the structures of the chemical compounds of the galanthamine library.
Figure 4:
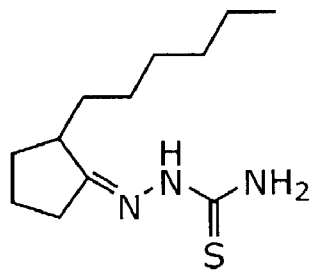
FIG. 4 is an illustration of the chemical structures of three chemical compounds that were assayed for their ability to affect host cell invasion by *Toxoplasma gondii*, and their inhibitory concentrations.
Figure 4:
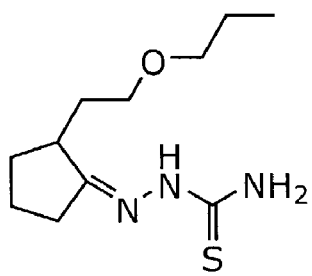
Figure 4:
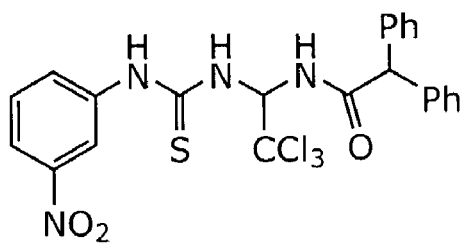
Figure 5:
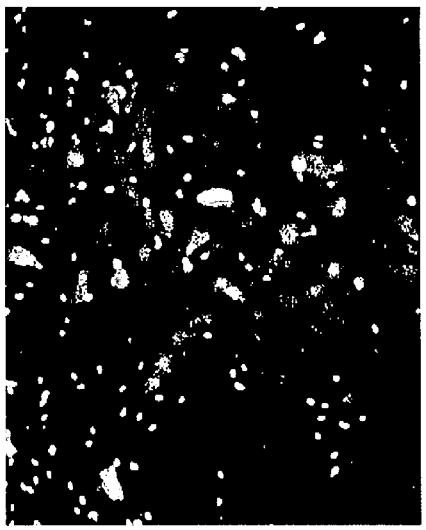
FIG. 5 is a photograph of an image taken through a fluorescent microscope showing parasites invading a host cell.
Figure 5:
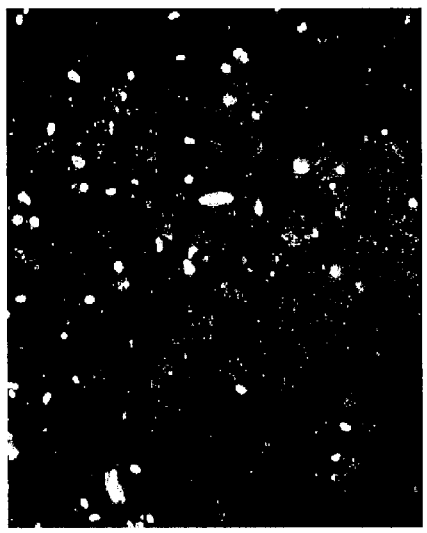
Figure 5:
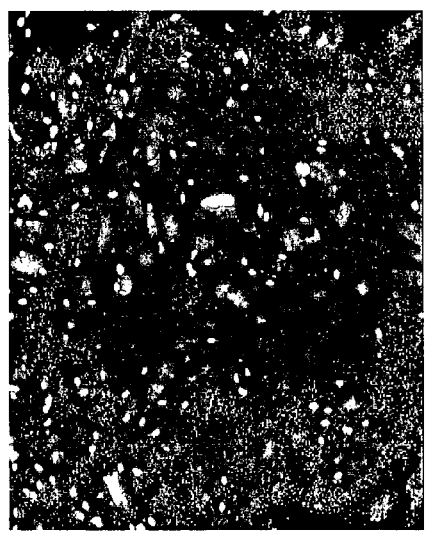
Figure 6A:
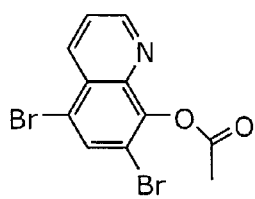
FIG. 6A–6O shows the chemical structure of various modulators of Apicomplexan parasitic infection.
Figure 6A:
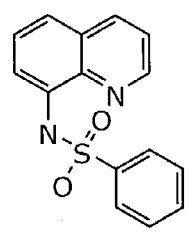
Figure 6A:
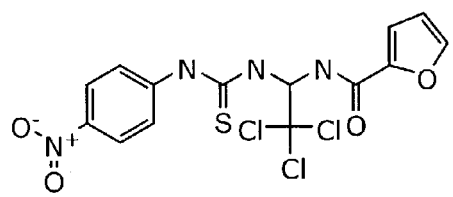
Figure 6A:
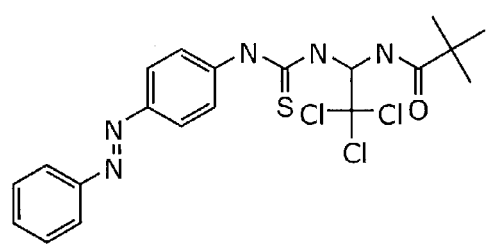
Figure 6A:
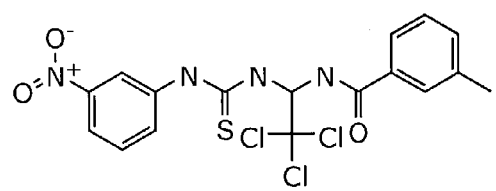
Figure 6A:
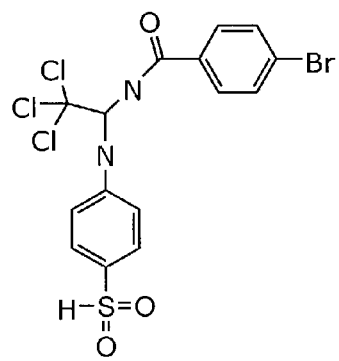
Figure 6A:
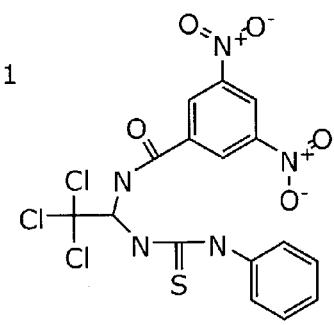
Figure 6A:
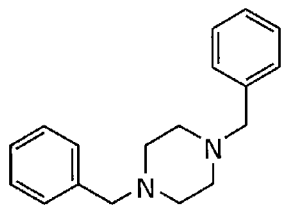
Figure 6A:
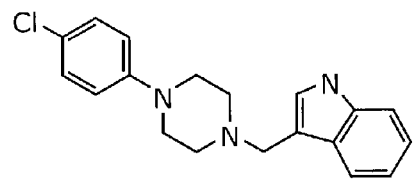
Figure 6A:
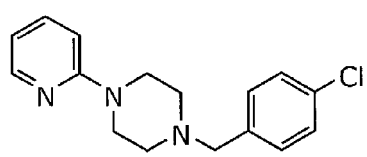
Figure 6B:
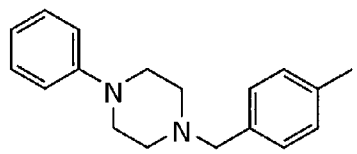
Figure 6B:
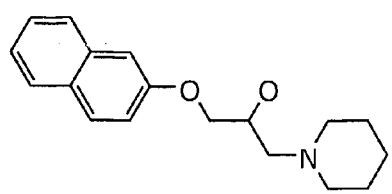
Figure 6B:
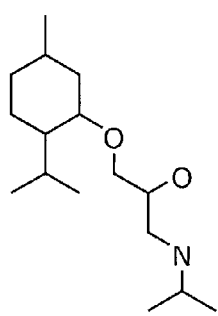
Figure 6B:
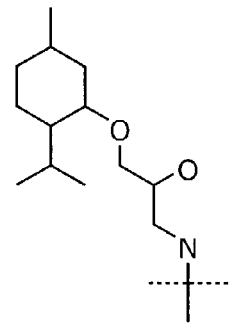
Figure 6B:
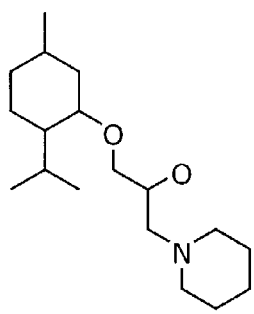
Figure 6B:
Figure 6B:
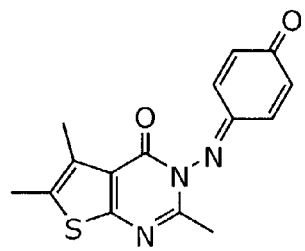
Figure 6B:
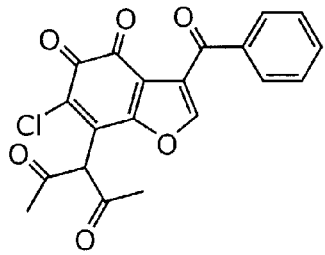
Figure 6B:
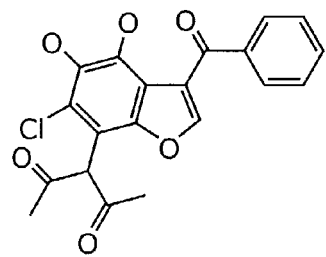
Figure 6B:
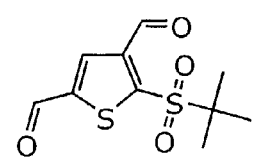
Figure 6C:
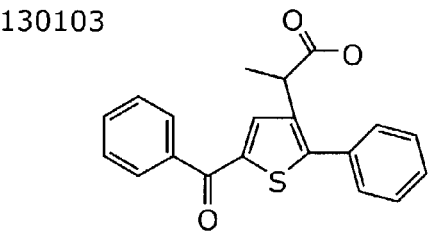
Figure 6C:
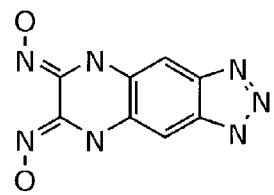
Figure 6C:
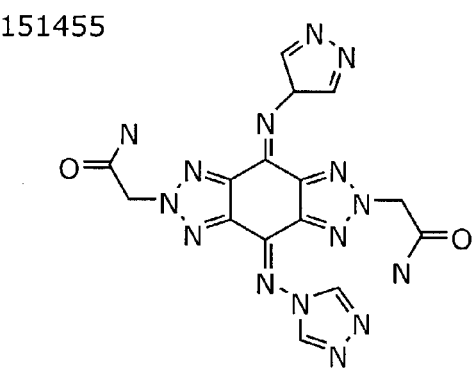
Figure 6C:
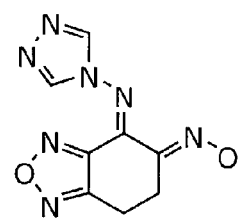
Figure 6C:
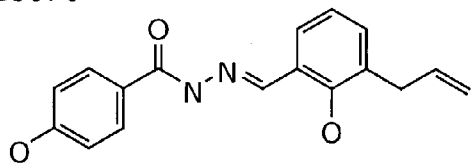
Figure 6C:
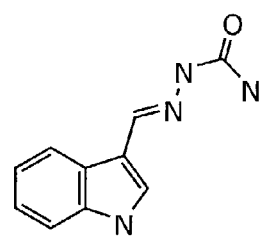
Figure 6C:
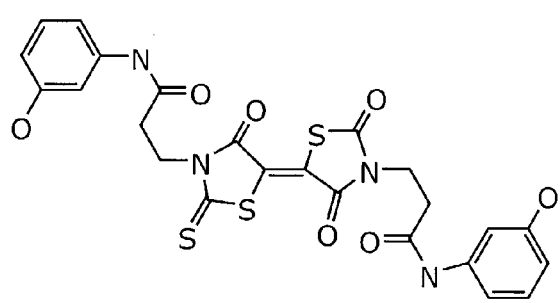
Figure 6C:
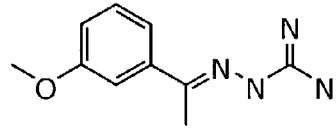
Figure 6C:
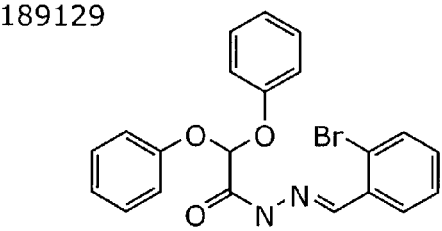
Figure 6C:
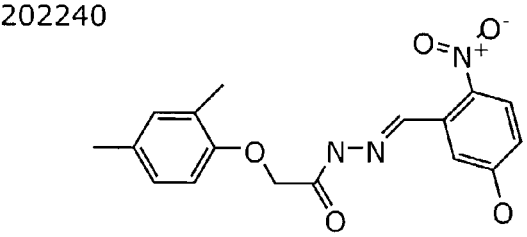
Figure 6D:
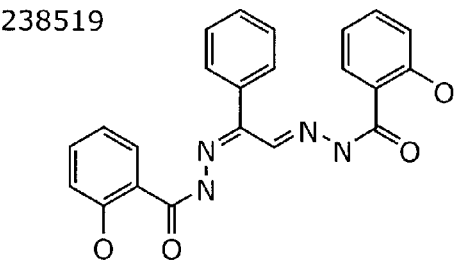
Figure 6D:
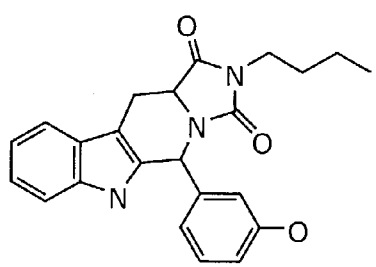
Figure 6D:
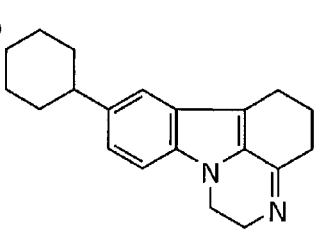
Figure 6D:
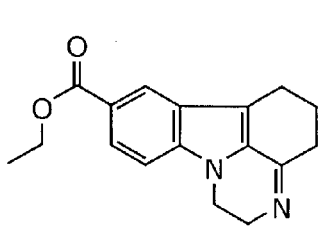
Figure 6D:
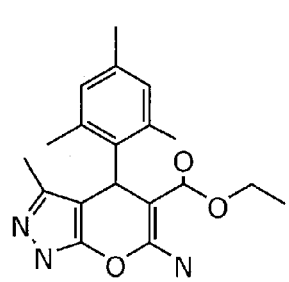
Figure 6D:
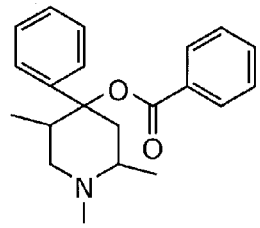
Figure 6D:
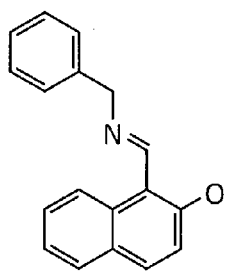
Figure 6D:
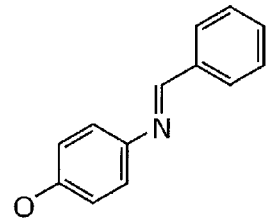
Figure 6D:
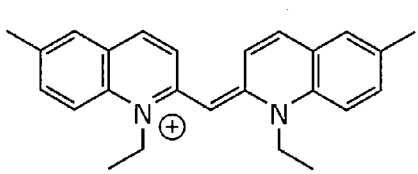
Figure 6D:
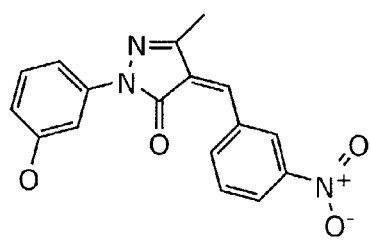
Figure 6E:
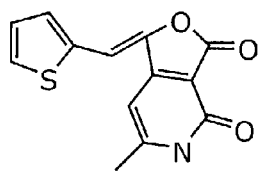
Figure 6E:
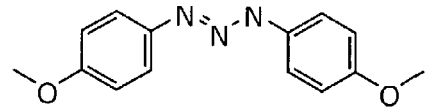
Figure 6E:
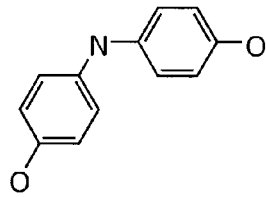
Figure 6E:
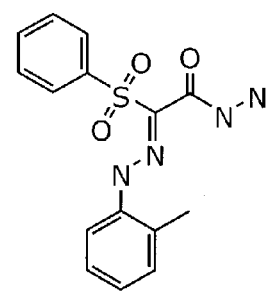
Figure 6E:
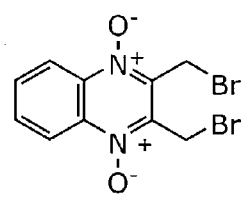
Figure 6E:
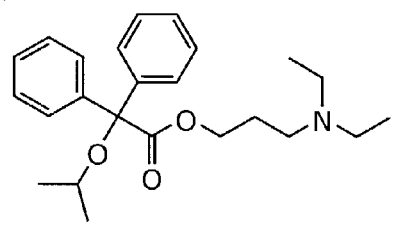
Figure 6E:
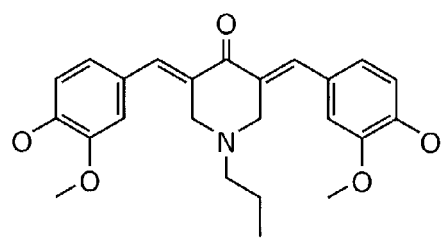
Figure 6E:
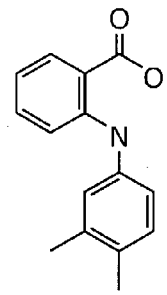
Figure 6E:
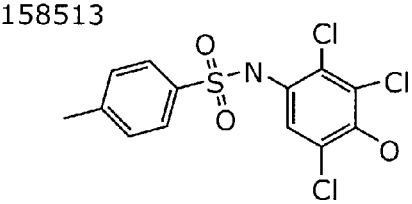
Figure 6E:
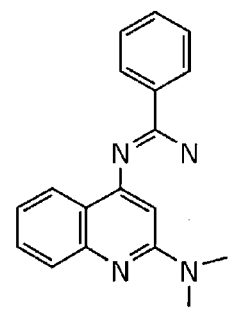
Figure 6F:
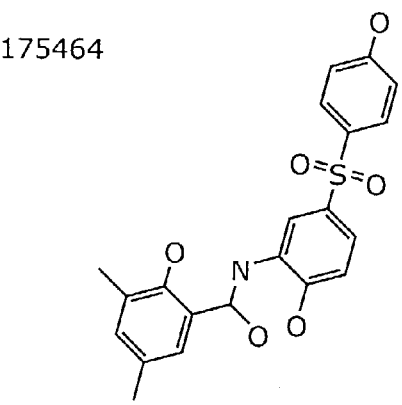
Figure 6F:
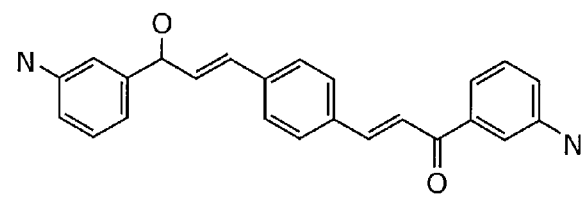
Figure 6F:
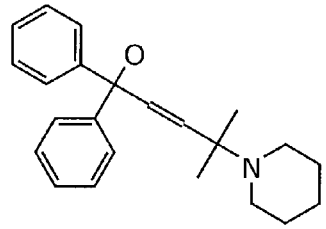
Figure 6F:
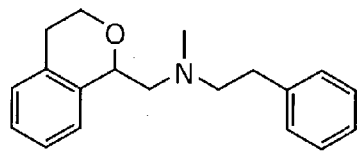
Figure 6F:
Figure 6F:
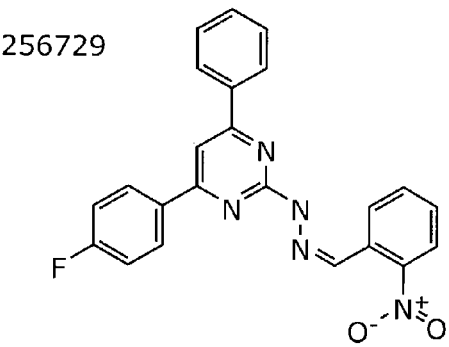
Figure 6F:
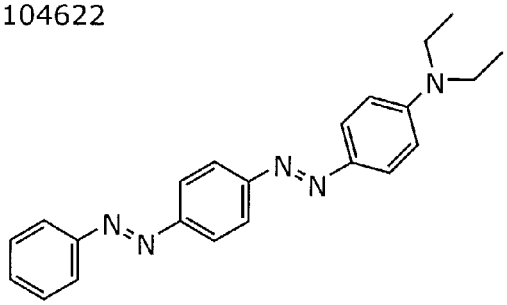
Figure 6F:
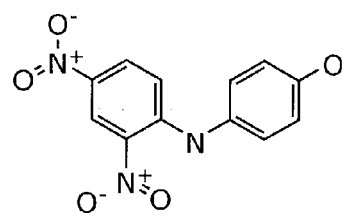
Figure 6F:
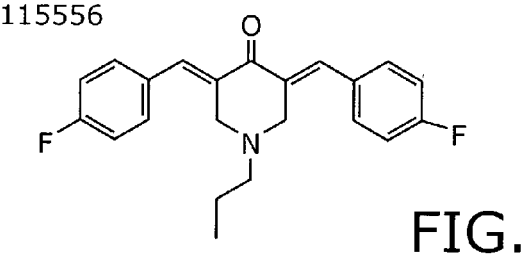
Figure 6F:
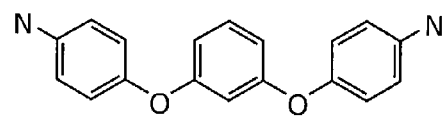
Figure 6G:
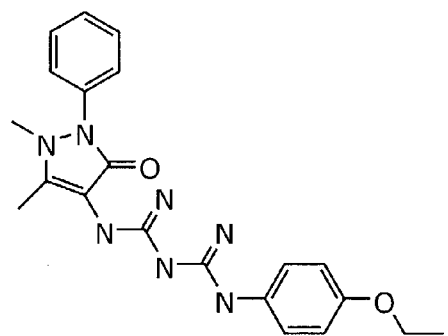
Figure 6G:
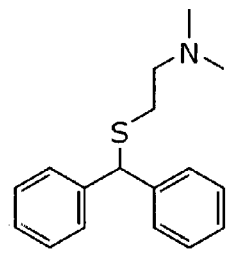
Figure 6G:
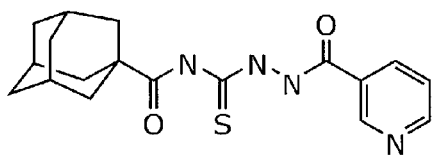
Figure 6G:
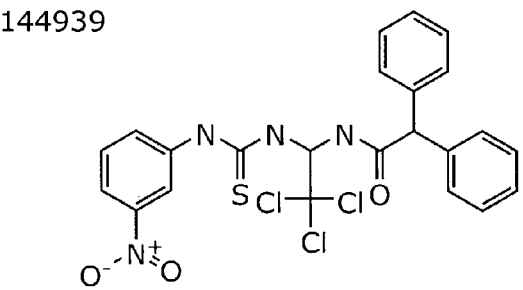
Figure 6G:
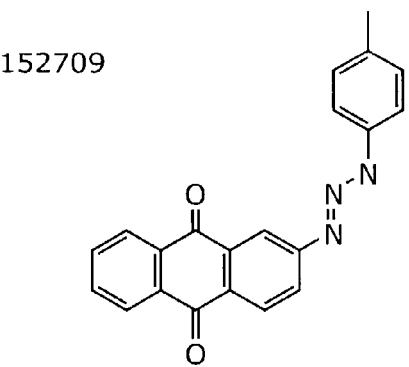
Figure 6G:
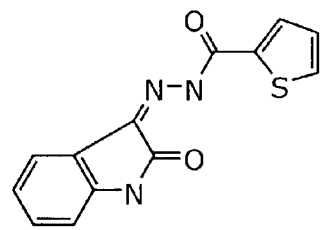
Figure 6G:
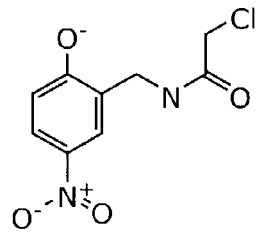
Figure 6G:
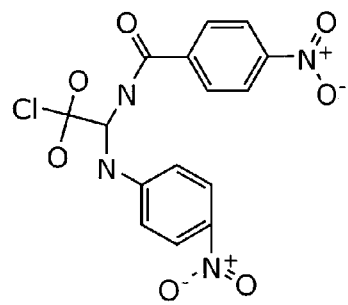
Figure 6H:
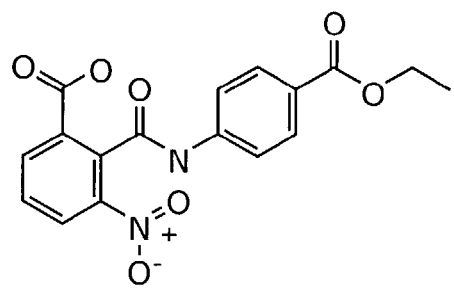
Figure 6H:
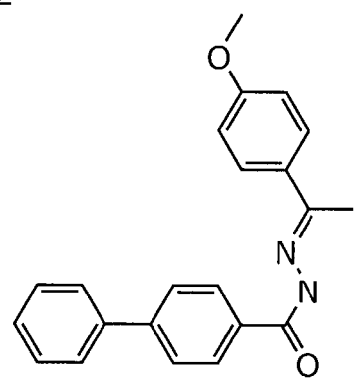
Figure 6H:
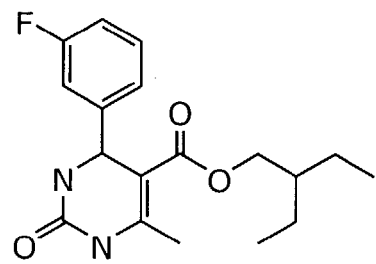
Figure 6I:
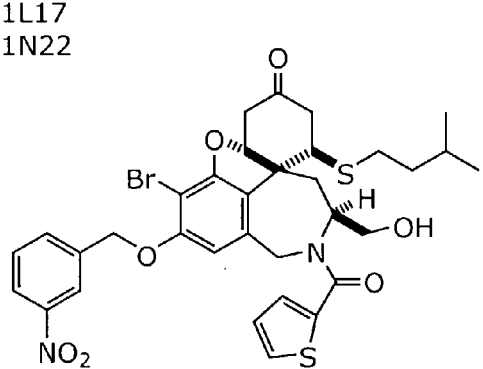
Figure 6I:
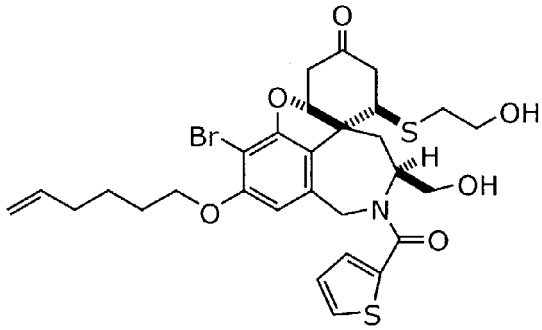
Figure 6I:
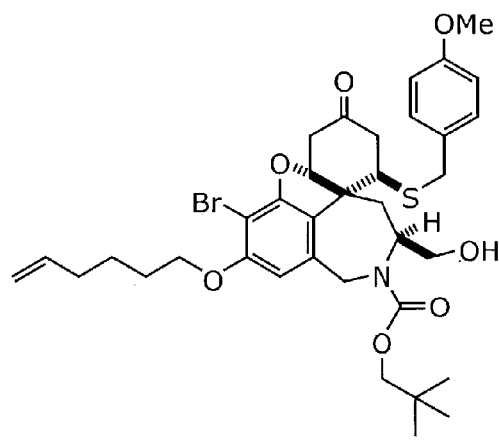
Figure 6I:
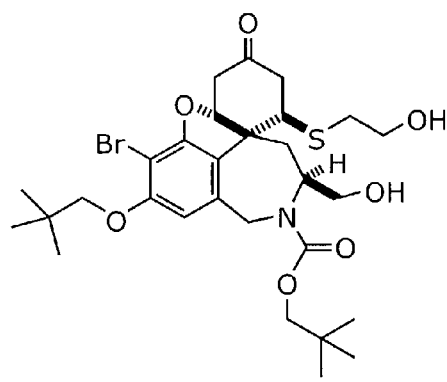
Figure 6I:
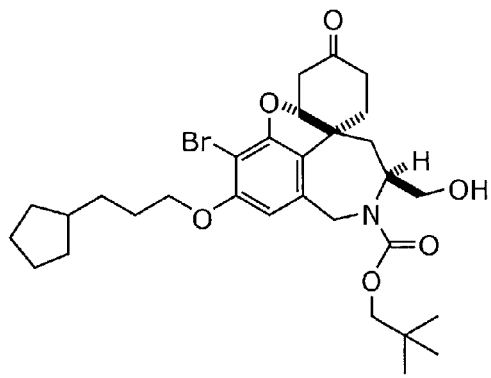
Figure 6I:
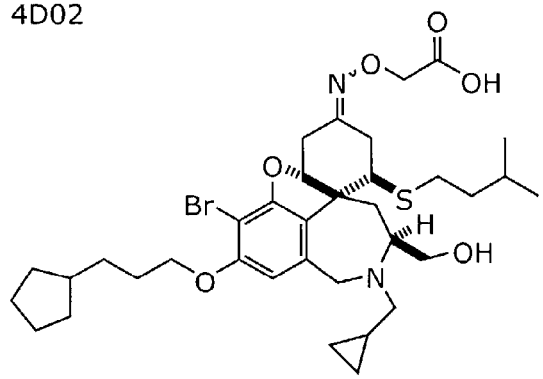
Figure 6J:
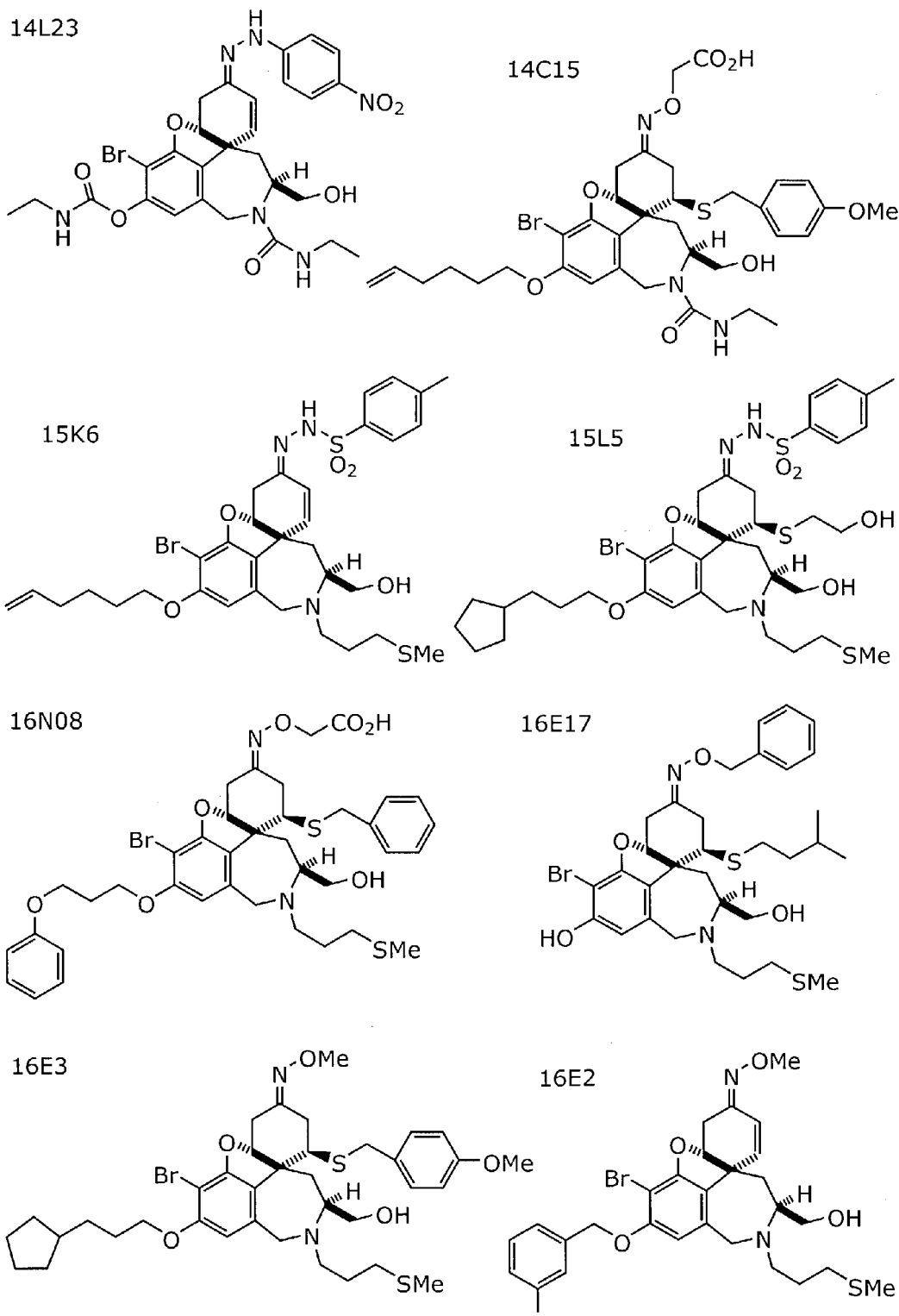
Figure 6K:
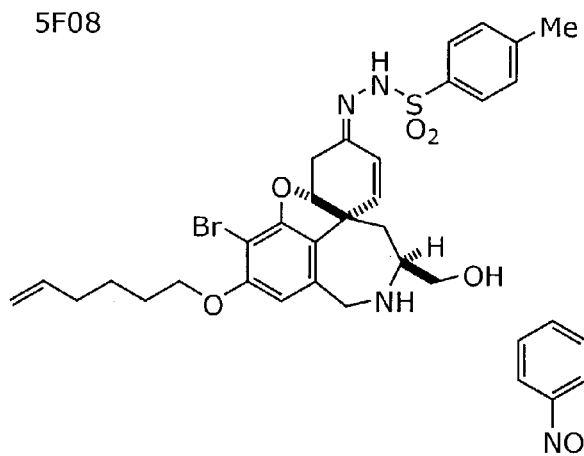
Figure 6K:
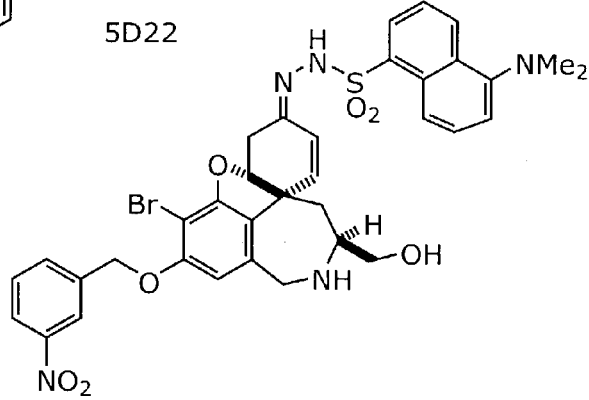
Figure 6K:
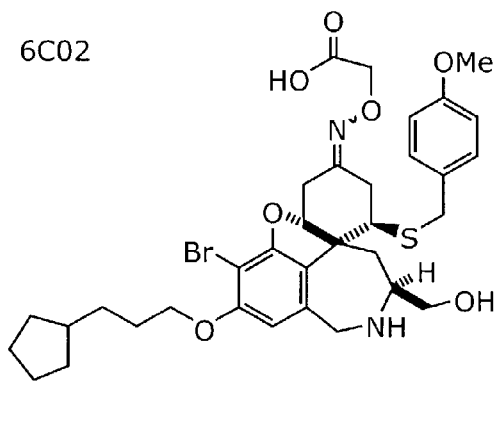
Figure 6K:
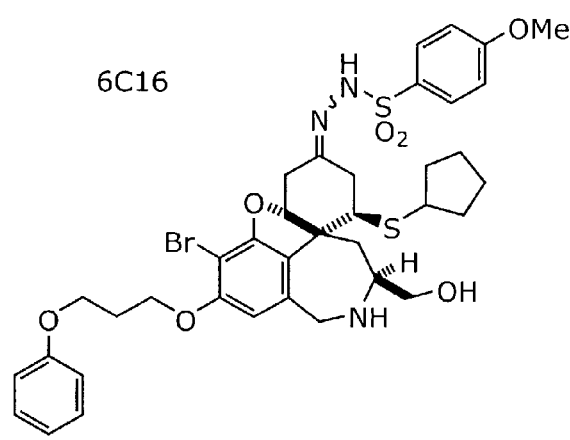
Figure 6K:
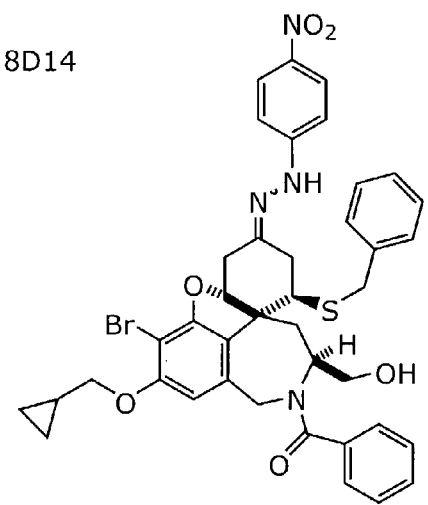
Figure 6K:
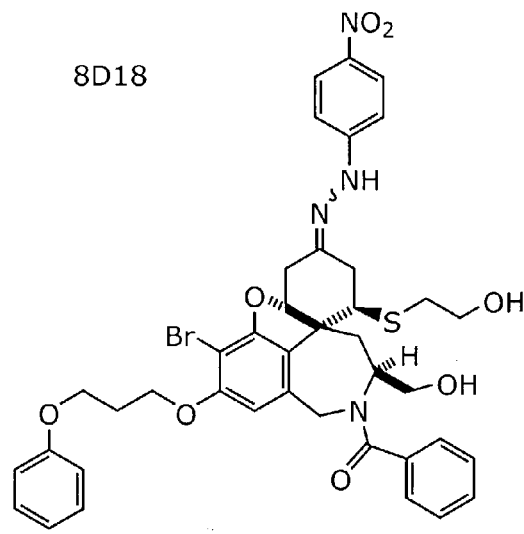
Figure 6L:
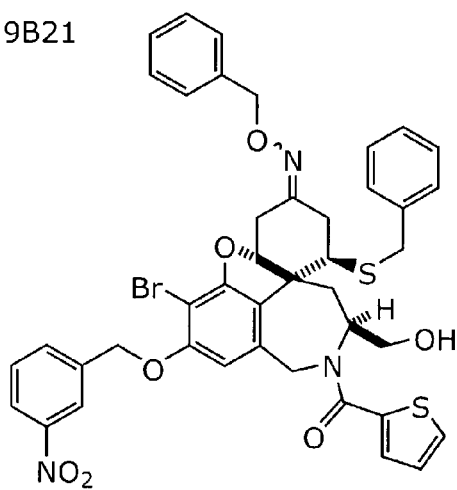
Figure 6L:
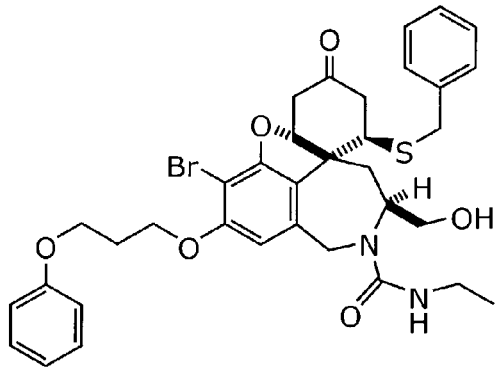
Figure 6L:
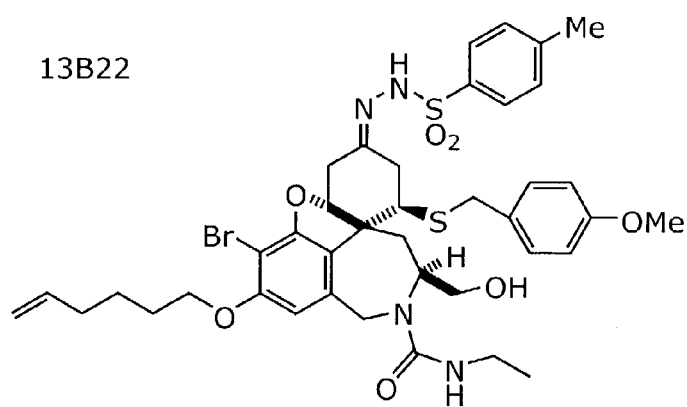
Figure 6L:
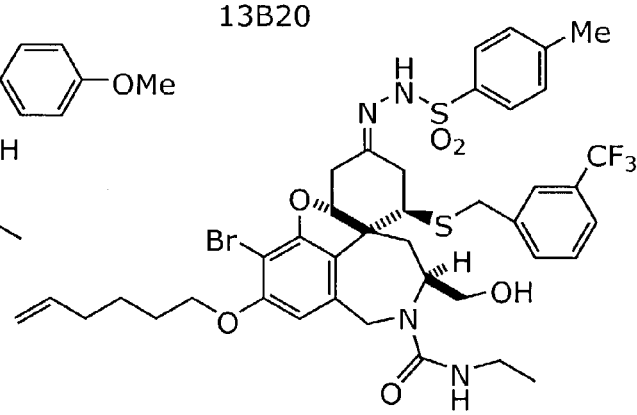
Figure 6L:
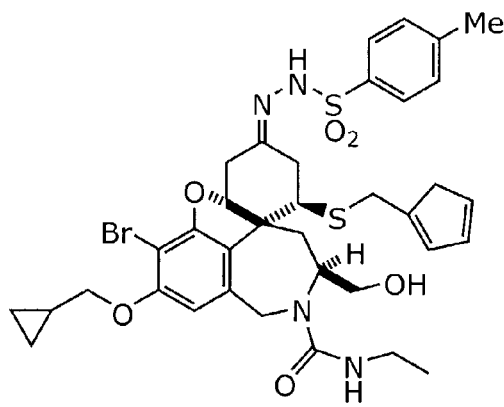
Figure 6L:
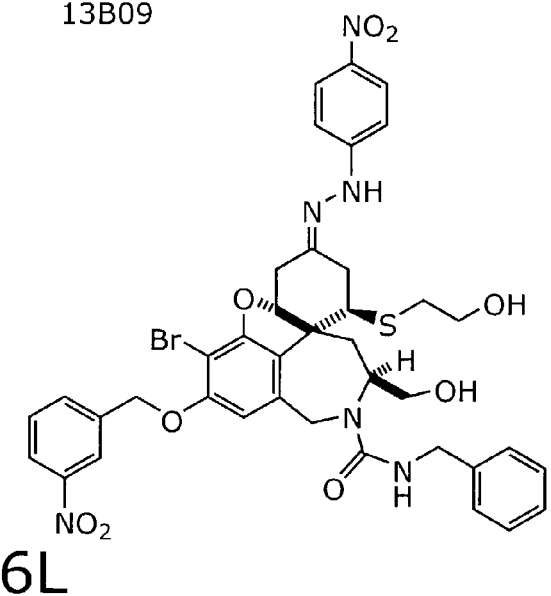
Figure 6M:
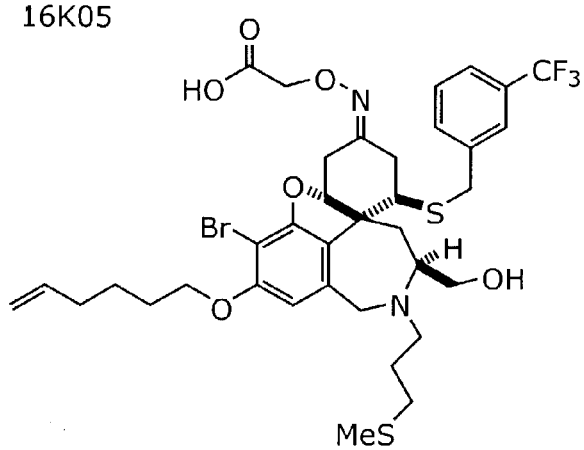
Figure 6M:
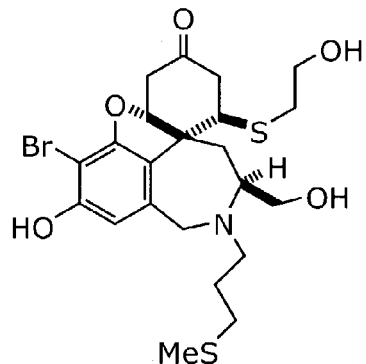
Figure 6M:
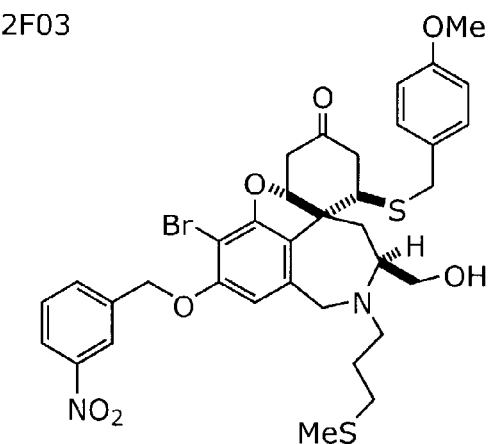
Figure 6M:
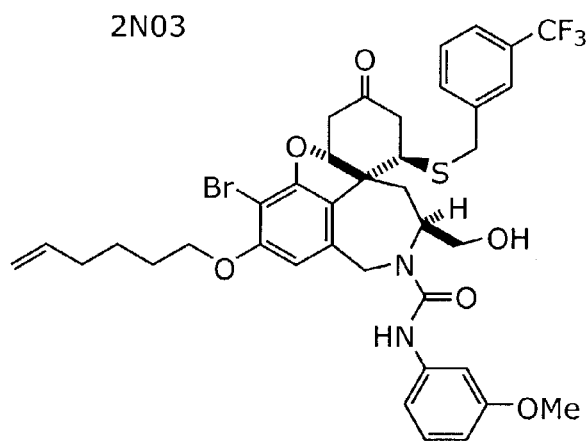
Figure 6M:
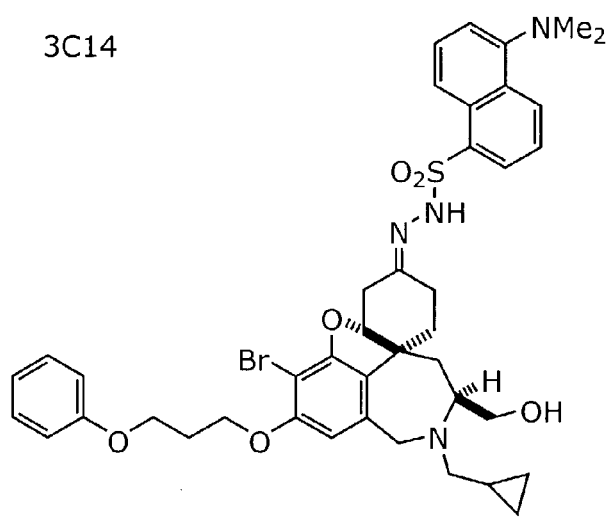
Figure 6M:
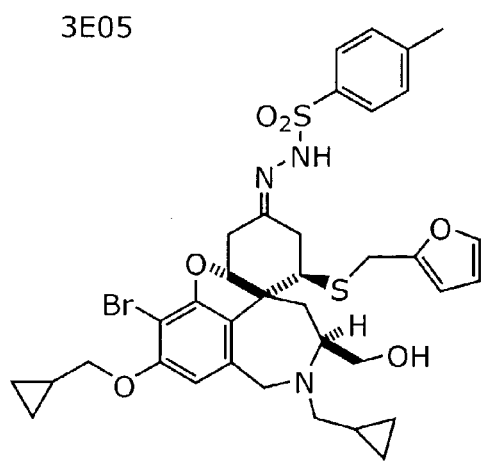
Figure 6N:
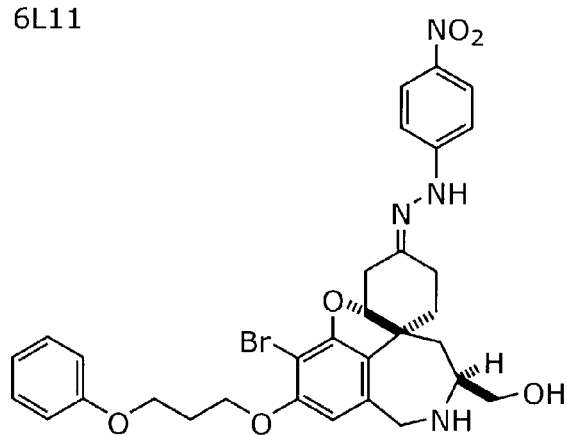
Figure 6N:
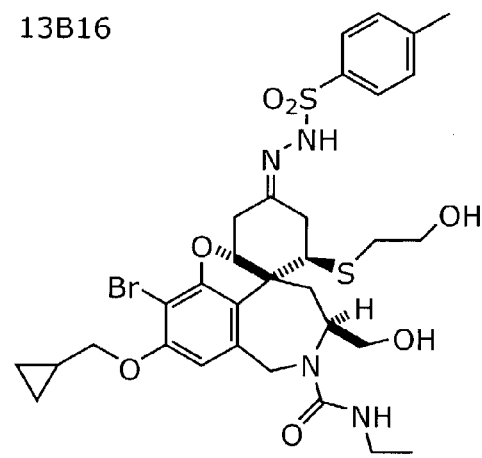
Figure 6N:
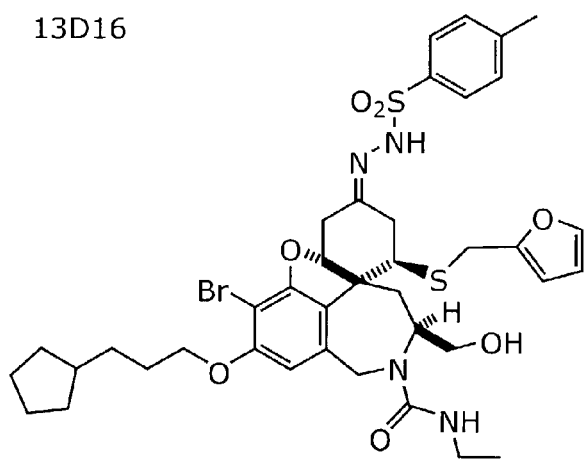
Figure 6N:
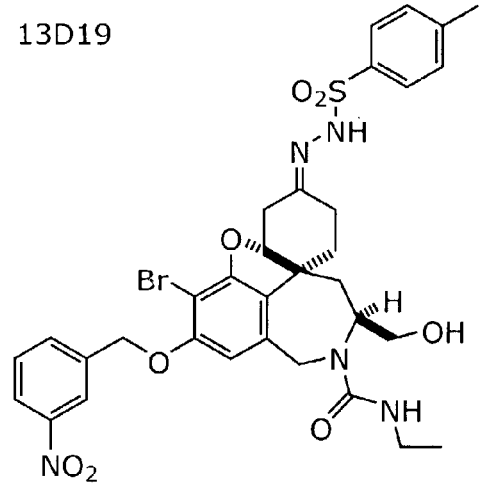
Figure 6N:
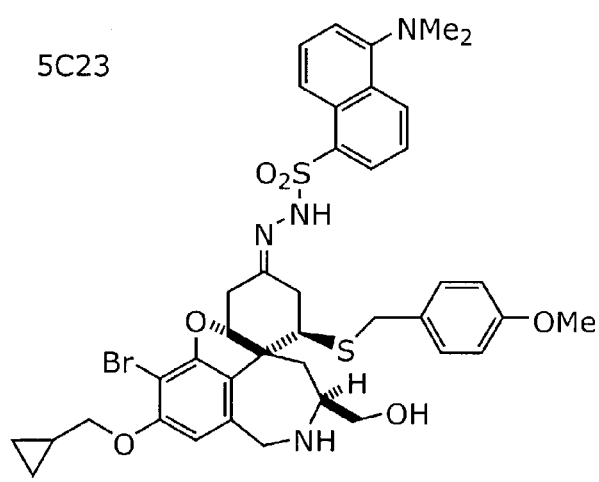
Figure 6O:
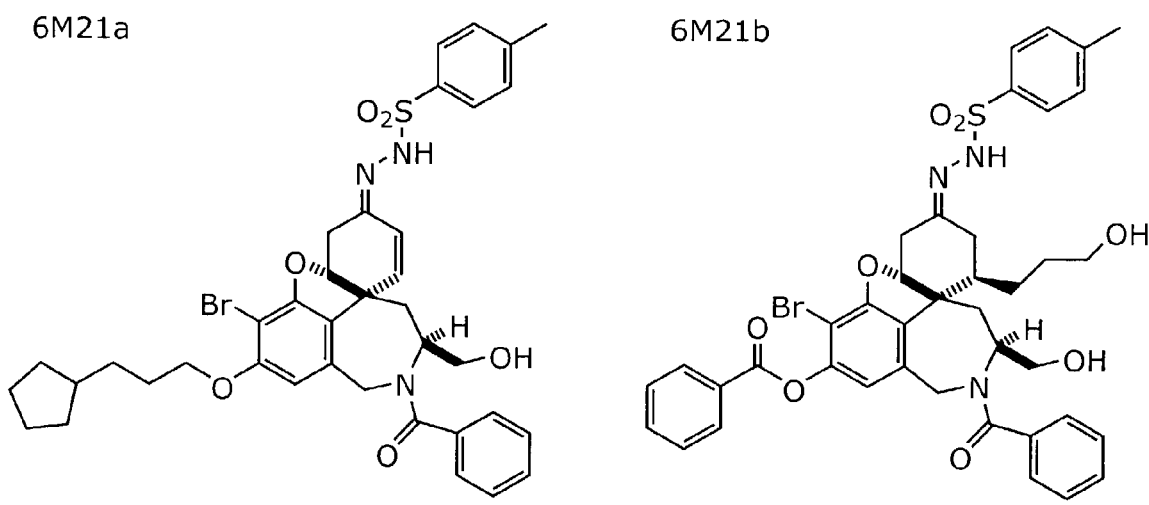

Such a screen as described above was carried out on several compounds from a library from Chembridge. Of course it will be appreciated that compounds from any of a number of libraries may be screened for activator or inhibitory activity using the present assay systems and methods. For example, the galanthamine library described in U.S. patent application Ser. No. 09/863,141 (see FIG. 3), incorporated herein by reference in its entirety. See also Pelish et al. Journal of the American Chemical Society (2001) 23(49): 6740–6741, Supporting Information, incorporated by reference herein in its entirety. As shown in FIG. 4 the compound F3 was inhibitory at 84 µM and the compound G2 was inhibitory at only 5 µM, while even 170 µM of F3* had no inhibitory effect on invasion of *T. gondii*.

Antibody Detection

The following protocol is carried out in all wells of a 384 well plate. The media covering a confluent monolayer of BSC-1 host cells was removed and replaced with a previously prepared solution of a test compound under examination in media. A solution of wild-type *T. gondii* tachyzoites (gift from Boris Striepen) (that are not labeled) is then added and the host cells and parasites are preincubated with the compound at a temperature at which invasion does not occur (20–22 C). After 15 minutes the assay plate was temperature shifted to 37° C., a temperature at which host cell invasion by the parasites occurs in the absence of compound. After 1 hour, excess parasites were removed by repeat rounds of washing. External parasites were immunostained using dye-conjugated anti SAG1 antibody. The dye is an Alexa dye (red) (Molecular Probes). The cells were then fixed by treating the cells for 30 minutes with formaldehyde/gluteraldehyde solution in Hanks buffer, which permeabilizes the cells. All parasites (internal and external) are then stained with a second SAG1 antibody that is labeled with a green fluorescent label.

Automated image acquisition and analysis techniques were used to determine the number of invaded parasites. In order to quantitate invasion, the number of parasites inside the cell, which are green only, are counted. Alternatively, the total number of external parasites (which are both red and green) is subtracted from the total number of parasites (both internal and external, which are labeled green and red). Compounds that lower the invasion level by 80% or raise it (by 2 fold) compared to control values (cells+parasites in the absence of test compound) are considered as preliminary hits in this assay. The SAG1 antibody may be used twice because there is enough SAG1 on the surface of these parasites that you do not saturate all of the sites with the first antibody.

FIG. 4 illustrates results as a control well from the above experiment. As noted in the figure, all parasites are labeled green, but only external parasites are labeled red. Quantitative and subtraction of total red from total green yields a number, which is representative of the total number of internal parasites.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

Example 2

Protozoal Modifying Agents

This example describes the identification of small molecule inhibitors and activators using the inventive assay systems and methods for protozoal cell invasion.

Methods

Cell Lines and Parasites

African Green Monkey BS-C-1 renal epithelial cells (CCL 26, American Type Culture Collection (ATCC), 10801 University Boulevard, Manassas, VA 20110–2209), were cultured in Dulbecco's Modified Eagle Medium (DMEM; Life Technologies, Gaithersburg, Md.) containing 10% fetal bovine serum (FBS; v/v). T. gondii tachyzoites (RH strain) stably expressing a tandem repeat of the yellow fluorescent protein (YFP; generous gift from B. Striepen) were cloned and cultured in human foreskin fibroblasts (CRL 1634, ATCC) under 20 µM chloramphenicol as previously described (Roos et al., (1994) Methods in Cell Biology 45, 27–63).

High-Throughput Invasion Assay

BS-C-1 cells were trypsinized, released into DMEM containing 10% (v/v) FBS, and dispensed into tissue culture-treated 384-well Special Optics plates (kindly provided by Coming Costar, Cambridge, Mass.) using a multidron dispenser (Thermo Labsystems Multidrop 384™ dispenser) (50 µl, 5×10³ cells per well). Cells were grown to confluence overnight at 37° C.

YFP-expressing parasites were freshly prepared by scraping a heavily infected monolayer of human foreskin fibroblasts off the flask and passing the cell suspension once through a 27 gauge needle. The released parasites were centrifuged 4 mm at 1000×g and resuspended in Hanks' balanced salt solution (HBSS; Life Technologies, Gaithersburg, Md., USA) containing 10 mM Hepes, pH 7.0 (HH) and 1% FBS (v/v). The suspension was filtered through 3 µm Nucleopore® filters (Whatman, Clifton, N. J., USA) to remove fibroblast debris, and diluted to 1–1.5×10⁷ parasites/ml in HH containing 1% FBS.

The culture medium was removed from the confluent BS-C-1 monolayers using a multichannel pipette and immediately replaced with 15 µl HBSS containing the compound to be tested. Parasites (10 µl) were added to each well and the plates incubated for 15 mm at 20–25° C., followed by 1–1.5 hr at 37° C. The final concentration of compound in each well was between 5 and 40 M. Wells were washed three times with HH containing 0.5% (w/v) bovine serum albumin (HHB; 30 µl/well), dispensing with the Multidrop 384 and aspirating with an Immunowash-16™ (Nalge-Nuno, Milwaukee, Wis.). Prior to fixation, any remaining extracellular parasites were immunostained using either Protocol A or Protocol B, as follows.

Protocol A: Infected monolayers were simultaneously incubated (15 mm, 25° C.) with a monoclonal antibody against the major 30 kDa surface protein of T. gondii (MAb 11–132, Argene, N. Massapequa, N.Y.) which had been directly conjugated to an Alexa Fluor® 546 dye as per the manufacturer's instructions (Molecular Probes, Eugene, Oreg.), and an Alexa 488-conjugated anti-mouse IgG (Molecular Probes) for 15 mm at RT. The Alexa 488-conjugated antibody served to augment the fluorescence of external parasites, a small percentage of which were found to have lost their YFP during manipulation of the plates. The optimal concentration ratio of the 2 antibodies was determined empirically prior to use in the screens.

Protocol B: Infected monolayers were incubated with MAb 11–132 (Argene, N. Massapequa, N.Y.) for 15 min at RT. Wells were washed twice with 50 µl HH prior to adding a mixture of Alexa 488-conjugated anti-mouse IgG and Alexa 546-conjugated anti-mouse IgG (Molecular Probes) for 15 min at RT. The optimal concentration ratio of the 2 secondary antibodies was determined empirically.

Following Protocol A or B, cells were washed twice with 50 µl HH, and fixed with HBSS containing 3.1% (v/v) formaldehyde and 0.06% (v/v) glutaraldehyde for 30 min at RT. Fixed monolayers were washed once with HH prior to adding phosphate-buffered saline (PBS) containing 75% (v/v) glycerol and 0.05% (v/v) sodium azide. Plates stored at 4° C. in the dark were stable for more than 1 month.

Gliding Motility Assay

Syringe-released parasites are filtered through a 3 µm Nucleopore filter, centrifuged at 1000×g for 4 min, and resuspended to 1×10⁷ tachyzoites/ml in HH containing 1% FCS (v/v). Parasites (10 .mu.l) are pretreated with 15 µl compounds in HBSS for 15 min at RT, then added to individual wells of a Black/Clear Optilux™ 384-well plate (BD Falcon, Bedford, Mass.), which has been precoated for 60 min with 100 µg/ml bovine serum albumin in PBS. The plate is incubated for 30 min at 37° C., and the trails (deposited by parasites that move during that time) are fixed with PBS containing 2.5% formaldehyde (v/v) for 10 min, 25° C. Wells are rinsed with PBS, and blocked for 10 min in PBS containing 0.5% (w/v) bovine serum albumin. Trails are visualized by sequential incubation with MAb 11–132 (2.5 µg/ml), and Alexa 488-conjugated anti-mouse IgG (20 µg/ml). The plates are observed on a Nikon TE300 inverted microscope (20×objective) using Nikon filter cube BE2C ($\alpha_{ex}$=465–495 nm). $\alpha_{em}$=515–595 nm). Fluorescence images are captured using a SpotRT monochrome camera driven by Spot v. 3.01 (AppleEvent) software (Diagnostic Instruments Inc., Sterling Heights Mich.) and processed post-capture using Adobe Photoshop™ 6.0 (Adobe Systems Inc., Mountain View, Calif.).

Use of Labeled Protozoa

The following protocol was carried out in all wells of a 384 well plate. The media covering a confluent monolayer of host cells was removed and replaced with a previously prepared solution of a test compound in media. The host cells were BSC-1 cells, a monkey kidney cell line (however, any host cell may be used because Toxoplasma gondii can invade essentially any nucleated cell). A solution of T. gondii tachyzoites (gift from Boris Striepen) expressing the yellow fluorescent protein was added and the host cells and labeled parasites were preincubated with the compound at a temperature at which invasion does not occur (20–22° C.). After 15 minutes, the assay plate was temperature shifted to 37° C., a temperature at which host cell invasion by the parasites occurs in the absence of compound. After 1 hour, excess parasites were removed by repeat rounds of washing. External parasites are immunostained using dye-conjugated anti-SAG1 antibody. The dye was an Alexa dye (red) (Molecular Probes). The cells were then fixed by treating the cells for 30 minutes with formaldehyde/gluteraldehyde solution in Hanks buffer.

Automated image acquisition and analysis techniques were used to determine the number of invaded parasites. In order to quantitate invasion, the total number of green fluorescent parasites associated with the cells (inside+outside) was counted using MetamorphHT® image analysis software. The total number of external parasites (red+green) was also determined. The number of red parasites was then subtracted from the number of green parasites to yield the total number of invaded parasites in each field. The number of invaded parasites in four different fields per well was determined, and averaged. Compounds that inhibit invasion by >80% (relative to untreated controls) are considered inhibitors, and compounds that increase invasion relative to controls by at least 2-fold are considered enhancers.

Such a screen as described above was carried out on several compounds from a library from Chembridge (San Diego, Calif.). Of course, it will be appreciated that compounds from any of a number of compounds and/or libraries may be screened for inhibitory or enhancer activity using the present assay systems and methods. For example, the galanthamine-like compounds described in Supporting Information published by Journal of the American Chemical Society in conjunction with Pelish, H. E. et al., (2001) J. Am. Chem. Soc. 123:6740–6741 (Supporting Information) incorporated herein by reference in its entirety, was also screened.

RESULTS

Compounds identified using the assays are provided in FIG. 6 (panels A–N) and the identities of the compounds as inhibitors of invasion or enhancers of invasion are provided in Tables 1 and 2 respectively.

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

What is claimed is:

1. A method for preventing an Apicomplexan parasitic infection, comprising: administering to a cell in need of such treatment, an effective amount of an Apicomplexan parasite inhibitor to prevent Apicomplexan parasitic infection in the cell, wherein the Apicomplexan parasite inhibitor is selected from the group consisting of molecules numbered 108296, 244378, 143088, 143267, 144939, 157591, 157808, 156079, 267405, 118793, 137846, 137861, 144146, 115556, 256729, 108343, 156579, 158513, 141852, 235236, 152813, 102260 as depicted in FIGS. 6A–6G and listed in Table 1.

2. The method of claim 1, wherein the Apicomplexan parasite inhibitor is an inhibitor of invasion.

3. The method of claim 1, wherein the Apicomplexan parasite inhibitor is an Apicomplexan parasite toxin.

4. The method of claim 3, wherein the Apicomplexan parasite toxin is an external parasite toxin.

5. The method of claim 3, wherein the Apicomplexan parasite toxin is an internal parasite toxin.

6. The method of claim 1, wherein the cell is at risk of infection with an Apicomplexan parasite selected from the group consisting of: *Toxoplasma, Plasmodium, Eimeria, Theileria, Babesia, Sarcocystis*, and *Cryptosporidium*.

7. The method of claim 1, wherein the cell is at risk of infection with *Toxoplasma gondii*.

8. The method of claim 1, wherein the cell is a mammalian cell.

9. The method of claim 1, wherein the cell is a human cell.

10. The method of claim 1, wherein the cell is an avian cell.

11. The method of claim 1, wherein the cell is a cultured cell.

* * * * *